(12) United States Patent
Fensome et al.

(10) Patent No.: US 7,268,149 B2
(45) Date of Patent: Sep. 11, 2007

(54) CYCLOTHIOCARBAMATE DERIVATIVES AS PROGESTERONE RECEPTOR MODULATORS AND METHODS OF TREATING SKIN DISORDERS

(75) Inventors: Andrew Fensome, Wayne, PA (US); Diane Deborah Harrison, Villanova, PA (US); Richard Craig Winneker, Penllyn, PA (US); Puwen Zhang, Audubon, PA (US); Jeffrey Curtis Kern, Gilbertsville, PA (US); Eugene Anthony Terefenko, Quakertown, PA (US)

(73) Assignee: Wyeth, Madison, NJ (US)

( * ) Notice: Subject to any disclaimer, the term of this patent is extended or adjusted under 35 U.S.C. 154(b) by 311 days.

(21) Appl. No.: 10/601,968

(22) Filed: Jun. 23, 2003

(65) Prior Publication Data

US 2004/0014798 A1 Jan. 22, 2004

Related U.S. Application Data

(60) Provisional application No. 60/391,885, filed on Jun. 25, 2002.

(51) Int. Cl.
*A61K 31/4704* (2006.01)
*A61K 31/137* (2006.01)

(52) U.S. Cl. .................... 514/312; 514/653

(58) Field of Classification Search ............ 514/230.3, 514/230.8, 414, 418, 336, 426, 649, 650, 514/312, 653, 212, 284, 311, 313, 314
See application file for complete search history.

(56) References Cited

U.S. PATENT DOCUMENTS

| | | | |
|---|---|---|---|
| 6,355,648 B1 | 3/2002 | Fensome et al. | |
| 6,407,101 B1 | 6/2002 | Collins et al. | |
| 6,436,929 B1 | 8/2002 | Zhang et al. | |
| 6,462,038 B1 * | 10/2002 | Higuchi et al. | 514/224.5 |
| 6,521,657 B2 | 2/2003 | Fensome et al. | |
| 6,566,372 B1 | 5/2003 | Zhi et al. | |
| 6,583,145 B1 | 6/2003 | Fensome et al. | |
| 6,964,973 B2 * | 11/2005 | Zhi et al. | 514/312 |
| 2002/0169198 A1 | 11/2002 | Fensome et al. | |
| 2003/0083322 A1 | 5/2003 | Kraemer et al. | |
| 2003/0087925 A1 | 5/2003 | O'Neill et al. | |
| 2003/0092711 A1 | 5/2003 | Zhang et al. | |
| 2003/0130505 A1 | 7/2003 | Zhi et al. | |

FOREIGN PATENT DOCUMENTS

| | | |
|---|---|---|
| GB | 2310660 A | 9/1997 |
| WO | WO-85/00519 A | 2/1985 |
| WO | WO 00/66555 A1 | 11/2000 |
| WO | WO 00/66570 A1 | 11/2000 |
| WO | WO-00/66571 A | 11/2000 |
| WO | WO 00/66581 A1 | 11/2000 |
| WO | WO-01/15108 A2 | 3/2001 |
| WO | WO-01/77100 A2 | 10/2001 |

OTHER PUBLICATIONS

Zhang et al., "Potent Nonsteroidal Progesterone Receptor Agonists: Synthesis and SAR study of 6-Aryl Benzoxazines", Bioorg. & Med. Chem. Lett., 12: 787-790 (Mar. 11, 2002).
Van Vloten et al., "The Effect of 2 Combined Oral Contraceptives Either Drospirenone or Cyproterone Acetate on Acne and Seborrhea", Cutis 69: 2 (Apr. 2002).
English translation of an Office Action dated Feb. 17, 2006 issued in counterpart Taiwanese Patent Application No. 92116986.
English translation of an Office Action dated Mar. 3, 2006 issued in counterpart Chinese Patent Application No. 03815194.4.
English translation of an Office Action dated Mar. 3, 2006 provided by our agent in counterpart Chilean Patent Application No. 1280/2003.
Fensome et al., "Synthesis and Structure-Activity Relationship of Novel 6-Aryl-1,4-Dihydrobenzo[d][1,3]oxazine-2-thiones as Progrsterone Receptor Modulators Leading to the Potent and Selective Nonsteroidal Progesterone Receptor Agonists Tanaproget", J. Med. Chem. 48:5092-5095 (2005).
Zhang et al., "Novel 6-Aryl-1,4-Dihydrobenzo[d][1,3]oxazine-2-thiones as Potent, Selective, and Orally Active Nonsteroidal Progesterone Receptor Agonists", Bioorg. & Med. Chem. Lett., 13: 1313-1316 (2003).

* cited by examiner

*Primary Examiner*—Brian Kwon
(74) *Attorney, Agent, or Firm*—Howson & Howson LLP; Arnold S. Milowsky

(57) ABSTRACT

The present invention provides methods of treating skin disorders includes delivering to a mammal a composition containing a compound of formula I, or tautomers thereof, in a regimen, wherein formula I is:

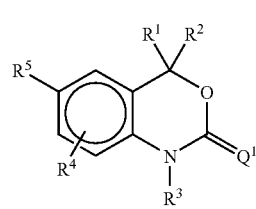

and wherein $R^1$-$R^5$ and $Q^1$ are defined as described herein. Specifically, methods for treating acne, hirsutism, and conditioning the skin are described. Also provided are novel PR modulators of formula II.

10 Claims, No Drawings

CYCLOTHIOCARBAMATE DERIVATIVES AS PROGESTERONE RECEPTOR MODULATORS AND METHODS OF TREATING SKIN DISORDERS

CROSS-REFERENCE TO RELATED APPLICATIONS

This is a non-provisional of U.S. patent application Ser. No. 60/391,885, filed Jun. 25, 2002.

BACKGROUND OF THE INVENTION

This invention relates to the treatment of skin disorders, including acne and hirsutism, and for conditioning the skin using compositions containing small molecules.

In view of the vast number of skin disorders diagnosed to date, a large amount of research has been conducted regarding the treatment of such disorders. Although many skin disorders are not considered dangerous, if left untreated irreversible physical scarring can result.

There are a number of treatments known to alleviate the symptoms of skin disorders, and include oral, intravenous, and topical delivery of compositions containing active agents, as well as surgical procedures such as laser therapy. However, such treatments may result in unpleasant side effects, tend to be suppressive rather than curative, are costly, and/or tend to worsen the disorder.

There exists a continued need in the art for alternative methods of alleviating the symptoms and/or resolving skin disorders and for conditioning the skin.

SUMMARY OF THE INVENTION

In one aspect, the invention provides methods of treating skin disorders including the step of delivering to a mammal a composition containing a compound of formula I, or tautomers thereof, and a physiologically compatible carrier, wherein formula I is:

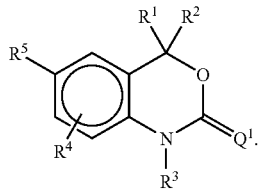

In a further aspect, the invention provides a method of treating acne including the step of delivering to a mammal a composition containing a compound of formula I.

In another aspect, the invention provides a method of treating hirsutism including the step of delivering to a mammal a composition containing a compound of formula I.

In yet a further aspect, the invention provides a method for conditioning the skin of a mammal, which includes the step of delivering to a mammal a composition containing a compound of formula I.

In still another aspect, the invention provides a compound of formula II useful for inducing contraception, hormone replacement therapy, conditioning the skin, and a variety of other conditions as described herein, wherein formula II is:

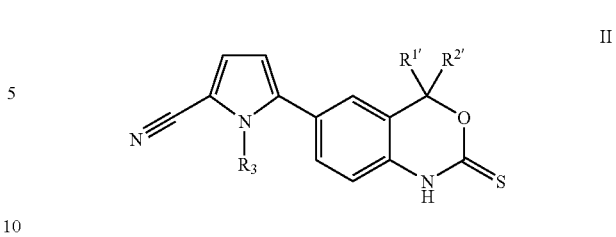

wherein $R^{1'}$ is selected from the group methyl, ethyl, trifluoromethyl; $R^{2'}$ is selected from the group methyl, ethyl, trifluoromethyl; or $R^{1'}$ and $R^{2'}$ are joined to form a spirocyclic ring containing 3 to 7 carbon atoms; and $R^{3'}$ is selected from the group $C_1$ to $C_4$ alkyl, and tautomers, prodrugs, metabolites, or pharmaceutically acceptable salts thereof.

Other aspects and advantages of the present invention are described further in the following detailed description of the preferred embodiments thereof.

DETAILED DESCRIPTION OF THE INVENTION

The present invention provides methods of treating skin disorders including delivering to a mammal a composition comprising a compound of formula I or formula II in a regimen.

The invention further provides novel progesterone receptor modulators of formula II, useful in the methods of treating skin disorders and for a variety of other purposes.

The term "tautomer" is meant to describe a compound which can exist in more than one isomeric state.

Preferably, the mammalian patient treated according to the present invention is a human, and more preferably a female.

The term "skin" is meant to describe the outer covering of a mammalian form including, without limitation, the epidermis, dermis, and subcutaneous tissues. Typically, the skin can include other components such as hair follicles and sweat glands.

The term "acne" is meant to include any skin disorder where a skin pore becomes blocked and/or thereby becomes inflamed. The term acne includes without limitation superficial acne, including comedones, inflamed papules, superficial cysts, and pustules; and deep acne, including deep inflamed modules and pus-filled cysts. Specific acne conditions can include, but are not limited to, acne vulgaris, acne comedo, papular acne, premenstrual acne, preadolescent acne, acne venenata, acne cosmetica, pomade acne, acne detergicans, acne excoriee, gram negative acne, acne rosacea, pseudofolliculitis barbae, folliculitis, perioral dermatitis, and hiddradenitis suppurativa.

The term "hirsutism" is meant to describe a skin disorder where an overgrowth of hair growth is observed in areas of the body which are not normally subject to excessive hair growth.

A number of skin disorders can be treated according to the methods of the present invention and include skin disorders of the hair follicles and sebaceous glands. Preferably, skin disorders such as acne and hirsutism, among others, can be treated according to the present invention.

Other skin disorders can include dry/chapped skin, seboria, psoriasis, or alopecia. The invention is also useful for treating the skin against the effects of environmental conditions. In addition, the compositions of the invention can be delivered in conjunction with other skin treatments, including laser surgery.

I. Progesterone Receptor Modulators

A. Compounds of Formula I Useful in Treatment of Skin Disorders

In one embodiment, the methods of the present invention include the delivery of compounds of the formula I, the preparation of which is described in International Patent Publication No. WO 00/66570 and hereby incorporated by reference. The compounds of formula I have the structure:

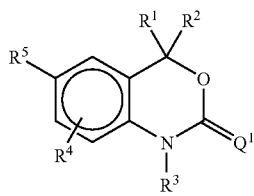

I wherein:

$R^1$ and $R^2$ are independent substituents selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, carbon-based heterocyclic ring having in its backbone 1 to 3 heteroatoms, substituted carbon-based heterocyclic ring having in its backbone 1 to 3 heteroatoms, $COR^A$, and $NR^B COR^A$;

or $R^1$ and $R^2$ are fused to form a ring selected from the group consisting of a), b) and c), wherein said ring is optionally substituted by from 1 to 3 substituents selected from the group consisting of H and $C_1$ to $C_3$ alkyl;

a) a carbon-based 3 to 8 membered saturated spirocyclic ring;

b) a carbon-based 3 to 8 membered spirocyclic ring having one or more carbon-carbon double bonds; and c) a 3 to 8 membered spirocyclic ring having in its backbone one to three heteroatoms selected from the group consisting of O, S and N;

$R^A$ is selected from the group consisting of H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, amino, $C_1$ to $C_3$ aminoalkyl, and substituted $C_1$ to $C_3$ aminoalkyl;

$R^B$ is selected from the group consisting of H, $C_1$ to $C_3$ alkyl, and substituted $C_1$ to $C_3$ alkyl;

$R^3$ is selected from the group consisting of H, OH, $NH_2$, $C_1$ to $C_6$ alkyl, substituted $C_1$ to $C_6$ alkyl, $C_3$ to $C_6$ alkenyl, substituted $C_3$ to $C_6$ alkenyl, alkynyl, substituted alkynyl, and $COR^C$;

$R^C$ is selected from the group consisting of H, $C_1$ to $C_4$ alkyl, substituted $C_1$ to $C_4$ alkyl, aryl, substituted aryl, $C_1$ to $C_4$ alkoxy, substituted $C_1$ to $C_4$ alkoxy, $C_1$ to $C_4$ aminoalkyl, and substituted $C_1$ to $C_4$ aminoalkyl;

$R^4$ is selected from the group consisting of H, halogen, CN, $NO_2$, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, and substituted $C_1$ to $C_6$ aminoalkyl;

$R^5$ is selected from the group consisting of (i) and (ii):

(i) a substituted benzene ring having the structure:

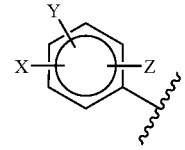

X is selected from the group consisting of halogen, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkyl, substituted $C_1$ to $C_3$ thioalkyl, $C_1$ to $C_3$ aminoalkyl, substituted $C_1$ to $C_3$ aminoalkyl, $NO_2$, $C_1$ to $C_3$ perfluoroalkyl, substituted $C_1$ to $C_3$ perfluoroalkyl, 5 or 6 membered carbon-based heterocyclic ring having in its backbone 1 to 3 heteroatoms, substituted 5 or 6 membered carbon-based heterocyclic ring having in its backbone 1 to 3 heteroatoms, $COR^D$, $OCOR^D$, and $NR^E COR^D$;

$R^D$ is selected from the group consisting of H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, and substituted $C_1$ to $C_3$ aminoalkyl;

$R^E$ is selected from the group consisting of H, $C_1$ to $C_3$ alkyl, and substituted $C_1$ to $C_3$ alkyl;

Y and Z are independent substituents selected from the group consisting of H, halogen, CN, $NO_2$, $C_1$ to $C_3$ alkoxy, substituted $C_1$ to $C_3$ alkoxy, $C_1$ to $C_4$ alkyl, substituted $C_1$ to $C_4$ alkyl, $C_1$ to $C_3$ thioalkyl, and substituted $C_1$ to $C_3$ thioalkyl; and b) a five or six membered carbon-based heterocyclic ring having in its backbone 1, 2, or 3 heteroatoms selected from the group consisting of O, S, SO, $SO_2$, and $NR^6$ and having one or two independent substituents selected from the group consisting of H, halogen, CN, $NO_2$, $C_1$ to $C_4$ alkyl, substituted $C_1$ to $C_4$ alkyl, $C_1$ to $C_3$ alkoxy, substituted $C_1$ to $C_3$ alkoxy, $C_1$ to $C_3$ aminoalkyl, substituted $C_1$ to $C_3$ aminoalkyl, $C_1$ to $C_3$ perfluoroalkyl, substituted $C_1$ to $C_3$ perfluoroalkyl, 5 or 6 membered carbon-based heterocyclic ring having in its backbone 1 to 3 heteroatoms, substituted 5 or 6 membered carbon-based heterocyclic ring having in its backbone 1 to 3 heteroatoms, $C_1$ to $C_3$ thioalkyl, substituted $C_1$ to $C_3$ thioalkyl, $COR^F$, and $NR^G COR^F$;

$R^F$ is selected from the group consisting of H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, and substituted $C_1$ to $C_3$ aminoalkyl;

$R^G$ is selected from the group consisting of H, $C_1$ to $C_3$ alkyl, and substituted $C_1$ to $C_3$ alkyl;

$R^6$ is selected from the group consisting of H, C to $C_3$ alkyl, and $C_1$ to $C_4$ $CO_2$alkyl;

$Q_1$ is selected from the group consisting of S, $NR^7$, and $CR^8 R^9$;

$R^7$ is selected from the group consisting of CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, carbon-based heterocyclic ring having in its backbone 1 to 3 heteroatoms, substituted carbon-based heterocyclic ring having in its backbone 1 to 3 heteroatoms, $SO_2 CF_3$, $OR^{11}$, and $NR^{11} R^{12}$;

$R^8$ and $R^9$ are independent substituents selected from the group consisting of H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, carbon-based heterocyclic ring having in its backbone 1 to 3 heteroatoms, substituted carbon-based heterocyclic ring having in its backbone 1 to 3 heteroatoms, $NO_2$, CN, and $CO_2R^{10}$;

$R^{10}$ is selected from the group consisting of $C_1$ to $C_3$ alkyl and substituted $C_1$ to $C_3$ alkyl;

or $CR^8R^9$ comprise a six membered ring having the structure:

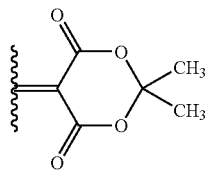

$R^{11}$ and $R^{12}$ are independently selected from the group consisting of H, $C_1$ to $C_6$ alkyl, substituted $C_1$ to $C_6$ alkyl, aryl, substituted aryl, carbon-based heterocyclic ring having in its backbone 1 to 3 heteroatoms, substituted carbon-based heterocyclic ring having in its backbone 1 to 3 heteroatoms, acyl, substituted acyl, sulfonyl, and substituted sulfonyl.

In another embodiment, the compound is of formula I:

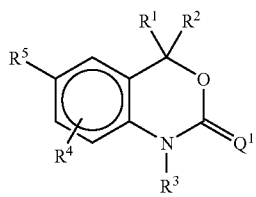

wherein:

$R^1$ and $R^2$ are independent substituents selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, carbon-based heterocyclic ring having in its backbone 1 to 3 heteroatoms, and substituted carbon-based heterocyclic ring having in its backbone 1 to 3 heteroatoms;

or $R^1$ and $R^2$ are fused to form a ring selected from the group consisting of a), b) and c), wherein said ring is optionally substituted by from 1 to 3 substituents selected from the group consisting of H and $C_1$ to $C_3$ alkyl;

a) a carbon-based 3 to 8 membered saturated spirocyclic ring;

b) a carbon-based 3 to 8 membered spirocyclic ring having one or more carbon-carbon double bonds; and c) a 3 to 8 membered spirocyclic ring having in its backbone one to three heteroatoms selected from the group consisting of O, S and N;

$R^3$ is H;

$R^4$ is selected from the group consisting of H, halogen, CN, $NO_2$, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, and substituted $C_1$ to $C_6$ aminoalkyl;

$R^5$ is selected from the group consisting of (i) and (ii):

(i) a substituted benzene ring having the structure:

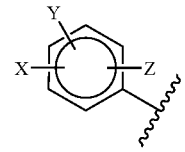

X is selected from the group consisting of halogen, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkyl, substituted $C_1$ to $C_3$ thioalkyl, $C_1$ to $C_3$ aminoalkyl, substituted $C_1$ to $C_3$ aminoalkyl, $NO_2$, $C_1$ to $C_3$ perfluoroalkyl, substituted $C_1$ to $C_3$ perfluoroalkyl, 5 or 6 membered carbon-based heterocyclic ring having in its backbone 1 to 3 heteroatoms, substituted 5 or 6 membered carbon-based heterocyclic ring having in its backbone 1 to 3 heteroatoms, $COR^D$, $OCOR^D$, and $NR^ECOR^D$;

$R^D$ is selected from the group consisting of H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, and substituted $C_1$ to $C_3$ aminoalkyl;

$R^E$ is selected from the group consisting of H, $C_1$ to $C_3$ alkyl, and substituted $C_1$ to $C_3$ alkyl;

Y and Z are independent substituents selected from the group consisting of H, halogen, CN, $NO_2$, $C_1$ to $C_3$ alkoxy, substituted $C_1$ to $C_3$ alkoxy, $C_1$ to $C_4$ alkyl, substituted $C_1$ to $C_4$ alkyl, $C_1$ to $C_3$ thioalkyl, and substituted $C_1$ to $C_3$ thioalkyl; and b) a five or six membered carbon-based heterocyclic ring having in its backbone 1, 2, or 3 heteroatoms selected from the group consisting of O, S, SO, $SO_2$, and $NR^6$ and having one or two independent substituents selected from the group consisting of H, halogen, CN, $NO_2$, $C_1$ to $C_4$ alkyl, substituted $C_1$ to $C_4$ alkyl, $C_1$ to $C_3$ alkoxy, substituted $C_1$ to $C_3$ alkoxy, $C_1$ to $C_3$ aminoalkyl, substituted $C_1$ to $C_3$ aminoalkyl, $C_1$ to $C_3$ perfluoroalkyl, substituted $C_1$ to $C_3$ perfluoroalkyl, 5 or 6 membered carbon-based heterocyclic ring having in its backbone 1 to 3 heteroatoms, substituted 5 or 6 membered carbon-based heterocyclic ring having in its backbone 1 to 3 heteroatoms, $C_1$ to $C_3$ thioalkyl, substituted $C_1$ to $C_3$ thioalkyl, $COR^F$, and $NR^GCOR^F$;

$R^F$ is selected from the group consisting of H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, and substituted $C_1$ to $C_3$ aminoalkyl;

$R^G$ is selected from the group consisting of H, $C_1$ to $C_3$ alkyl, and substituted $C_1$ to $C_3$ alkyl;

$R^6$ is selected from the group consisting of H, $C_1$ to $C_3$ alkyl, and $C_1$ to $C_4$ $CO_2$alkyl;

$Q_1$ is S.

In yet another embodiment, the compound is 6-(3-Chlorophenyl)-4,4-dimethyl-1,4-dihydro-benzo[d][1,3]oxazin-2-thione, 4-(4,4-Dimethyl-2-thioxo-1,4-dihydro-2H-benzo[d][1,3]oxazin-6-yl)-thiophene-2-carbonitrile, 3-(4,4-Dimethyl-2-thioxo-1,4-dihydro-2H-benzo[d][1,3]oxazin-6-yl)-5-fluorobenzonitrile, 3-(4,4-Dimethyl-2-thioxo-1,4-dihydro-2H-benzo[d][1,3]oxazin-6-yl)-benzonitrile, 6-(3-fluorophenyl)-4-methyl-1,4-dihydro-2H-3,1-benzoxazine-2-thione, 5-(4,4-Dimethyl-2-thioxo-1,4-dihydro-2H-3,1-benzoxazin-6-yl)-4-methylthiophene-2-carbonitrile, tert- Butyl 2-cyano-5-(4,4-dimethyl-2-thioxo-1,4-dihydro-2H-3,1-benzoxazin-6-yl)-1H-pyrrole-1-carboxylate, 5-(4,4-Dimethyl-2-thioxo-1,4-dihydro-2H-3,1-benzoxazin-6-yl)-1H-pyrrole-2-carbonitrile, [6-(4,4-dimethyl-2-thioxo-1,4-dihydro-2H-3,1-benzoxazin-6-yl)-pyridin-2-yl]acetonitrile, 5-(4,4-Dimethyl-2-thioxo-1,4-dihydro-2H-3,1-benzoxazin-6-yl)-1-methyl-1H-pyrrole-2-carbonitrile, 5-(4,4-dimethyl-2-thioxo-1,4-dihydro-2H-3,1-benzoxazin-6-yl)-1H-pyrrole-2-carbothiamide, 5-(4,4-Dimethyl-2-thioxo-1,4-dihydro-2H-benzo[d][1,3]oxazin-6-yl) thiophene-3-carbonitrile, 5-(4,4-dimethyl-2-thioxo-1,4-dihydro-2H-3,1-benzoxazin-6-yl)-1-ethyl-1H-pyrrole-2-carbonitrile, 4-(1,2-Dihydro-2-thioxospiro[4H-3,1-benzoxazin-4,1-cyclohexan]-6-yl)-2-thiophenecarbonitrile, 5-(4,4-Dimethyl-2-thioxo-1,4-dihydro-2H-3,1-benzoxazin-6-yl)-2-fluorobenzonitrile, 6-(5-Bromopyridin-3-yl)-4,4-dimethyl-1,4-dihydro-2H-3,1-benzoxazine-2-thione, 6-(3-Chloro-5-fluorophenyl)-4,4-dimethyl-1,4-dihydro-2H-3,1-benzoxazine-2-thione, 6-(3-Bromo-5-methylphenyl)-4,4-dimethyl-1,4-dihydro-2H-3,1-benzoxazine-2-thione, 6-(3-Bromo-5-trifluoromethoxyphenyl)-4,4-dimethyl-1,4-dihydro-2H-3,1-benzoxazine-2-thione, 3-(1,2-Dihydro-2-thioxospiro [4H-3,1-benzoxazine-4,1-cyclohexan]-6-yl)-5-fluorobenzonitrile, 3-(4,4-Dimethyl-2-thioxo-1,4-dihydro-2H-3,1-benzoxazin-6-yl)-5-methylbenzonitrile, 6-(3,5-Dichlorophenyl)-4,4-dimethyl-1,4-dihydro-2H-3,1-benzoxazine-2-thione, 5-(4,4-Dimethyl-1,2-thioxo-1,4-dihydro-2H-3,1-benzoxazin-6-yl) isophthalonitrile, 5-(4,4-Dimethyl-2-thioxo-2H-3,1-benzoxazin-6-yl)-2-furonitrile, 4,4-Diethyl-6-(3-nitrophenyl)-1,4-dihydro-2H-3,1-benzoxazine-2-thione, 6-(3-Chlorophenyl)-4-methyl-4-phenyl-1,4-dihydro-2H-3,1-benzoxazine-2-thione, 4-Allyl-6-(3-chlorophenyl)-4-methyl-1,4-dihydro-2H-3,1-benzoxazine-2-thione, 3-Chloro-5-(4,4-dimethyl-2-thioxo-1,4-dihydro-2H-3,1-benzoxazin-6-yl)benzonitrile, 6-(3,5-Difluorophenyl)-4,4-dimethyl-1,4-dihydro-2H-3,1-benzoxazine-2-thione, 6-(3-Fluoro-5-methoxyphenyl)-4,4-dimethyl-1,4-dihydro-2H-3,1-benzoxazine-2-thione, 3-(4,4-Dimethyl-2-thioxo-1,4-dihydro-2H-3,1-benzoxazin-6-yl)-5-methoxybenzonitrile, 6-(3-Fluorophenyl)-4,4-dimethyl-1,4-dihydro-2H-3,1-benzoxazine-2-thione, 6-[3-Fluoro-5-(trifluoromethyl)phenyl]-4,4-dimethyl-1,4-dihydro-2H-3,1-benzoxazine-2-thione,6-(2-Fluorophenyl)-4,4-dimethyl-1,4-dihydro-2H-3,1-benzoxazine-2-thione, 6-(3,4-Difluorophenyl)-4,4-dimethyl-1,4-dihydro-2H-3,1-benzoxazine-2-thione, 6-(4-Fluorophenyl)-4,4-dimethyl-1,4-dihydro-2H-3,1-benzoxazine-2-thione, 3-(4,4-Dimethyl-2-thioxo-1,4-dihydro-2H-3,1-benzoxazin-6-yl)-4-fluorobenzonitrile, 6-(2,3-Difluorophenyl)-4,4-dimethyl-1,4-dihydro-2H-3,1-benzoxazine-2-thione, 3-(8-Bromo-4,4-dimethyl-2-thioxo-1,4-dihydro-2H-3,1-benzoxazin-6-yl)-5-fluorobenzonitrile, 4,4-Dimethyl-6-(3-nitrophenyl)-1,4-dihydro-2H-3,1-benzoxazine-2-thione, 6-(3-Chlorophenyl)-4,4-diethyl-1,4-dihydro-2H-3,1-benzoxazine-2-thione, 6-(3-Methoxyphenyl)-4,4-dimethyl-1,4-dihydro-2H-3,1-benzoxazine-2-thione, 6-(2-Chlorophenyl)-4,4-dimethyl-1,4-dihydro-2H-3,1-benzoxazine-2-thione, 4-Benzyl-6-(3-chlorophenyl)-4-methyl-1,4-dihydro-2H-3,1-benzoxazine-2-thione, 6-(3-Bromo-5-fluorophenyl)-4,4-dimethyl-1,4-dihydro-2H-3,1-benzoxazine-2-thione, 5-(4,4-Dimethyl-2-thioxo-1,4-dihydro-2H-3,1-benzoxazin-6-yl) thiophene-2-carbonitrile, 3-Fluoro-5-(8-fluoro-4,4-dimethyl-2-thioxo-1,4-dihydro-2H-3,1-benzoxazin-6-yl)benzonitrile, 3-(1,2-Dihydro-2-thioxospiro[4H-3,1-benzoxazine-4,1-cyclohexan]-6-yl)benzonitrile, 5-(1,2-Dihydro-2-thioxospiro[4H-3,1-benzoxazine-4,1-cyclohexan]-6-yl)-4-methyl-2-thiophenecarbonitrile, 5-(1,2-Dihydro-2-thioxospiro[4H-3,1-benzoxazine-4,1-cyclohexan]-6-yl)-2-thiophenecarbonitrile, 6-(3-Chloro-4-fluorophenyl)-4,4-dimethyl-1,4-dihydro-2H-3,1-benzoxazine-2-thione, 5-(4,4-Dimethyl-2-thioxo-1,4-dihydro-2H-3,1-benzoxazin-6-yl)-4-propylthiophene-2-carbonitrile, 4-(4,4-Dimethyl-2-thioxo-1,4-dihydro-2H-3,1-benzoxazin-6-yl)-2-furonitrile, 4-Butyl-5-(4,4-dimethyl-2-thioxo-1,4-dihydro-2H-3,1-benzoxazin-6-yl) thiophene-2-carbonitrile, 6-(3-Bromophenyl)-4,4-dimethyl-1,4-dihydro-2H-3,1-benzoxazine-2-thione, and 2-(4,4-Dimethyl-2-thioxo-1,4-dihydro-2H-3,1-benzoxazin-6-yl) thiophene-3-carbonitrile, or a pharmaceutically acceptable salt, tautomer, metabolite, or prodrug thereof. Preferably, the compound is 5-(4,4-dimethyl-2-thioxo-1,4-dihydro-2H-3, 1-benzoxazin-6-yl)-1-methyl-1H-pyrrole-2-carbonitrile, or a pharmaceutically acceptable salt, tautomer, metabolite, or prodrug thereof.

B. Novel Progesterone Receptor Modulators of Formula II

The novel compounds of formula II are potent PR modulators. These compounds are used for contraception, in the treatment of fibroids, endometriosis, breast, uterine, ovarian and prostate cancer, hormone replacement therapy, and skin disorders.

Formula II is characterized by the structure:

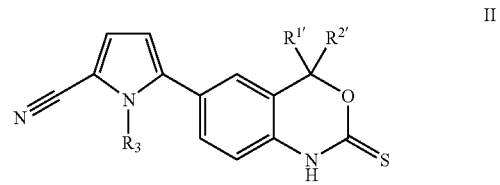

wherein $R^{1'}$ is selected from the group methyl, ethyl, trifluoromethyl; $R^{2'}$ is selected from the group methyl, ethyl, trifluoromethyl; or $R^{1'}$ and $R^{2'}$ are joined to form a spirocyclic ring containing 3 to 7 carbon atoms; and $R^{3'}$ is selected from the group $C_1$ to $C_4$ alkyl, and tautomers, prodrugs, metabolites, or pharmaceutically acceptable salts thereof.

Particularly desirable compounds of formula II include, 5-(4-ethyl-4-methyl-2-thioxo-1,4-dihydro-2H-3,1-benzoxazin-6-yl)-1-methyl-1H-pyrrole-2-carbonitrile, 5-(4,4-diethyl-2-thioxo-1,4-dihydro-2H-3,1-benzoxazin-6-yl)-1-methyl-1H-pyrrole-2-carbonitrile, 1-methyl-5-(2-thioxo-1,2-dihydrospiro[3,1-benzoxazine-4,1'-cyclobutan]-6-yl)-1H-pyrrole-2-carbonitrile, 1-methyl-5-(2-thioxo-1,2-dihydrospiro[3,1-benzoxazine-4,1'-cyclohexan]-6-yl)-1H-pyrrole-2-carbonitrile, 1-methyl-5-(2-thioxo-1,2-dihydrospiro[3,1-benzoxazine-4,1'-cyclopentan]-6-yl)-1H-pyrrole-2-carbonitrile, 1-methyl-5-[2-thioxo-4,4-bis(trifluoromethyl)-1,4-dihydro-2H-3,1-benzoxazine-6-yl]-1H-pyrrole-2-carbonitrile, pro drugs, metabolites, or pharmaceutically acceptable salts thereof. These compounds have been shown to act as competitive inhibitors of progesterone binding to the PR and act as potent agonists in functional assays as shown below.

The compounds utilized according to the present invention can contain one or more asymmetric centers and can thus give rise to optical isomers and diastereomers. While shown without respect to stereochemistry, the compounds can include optical isomers and diastereomers; racemic and resolved enantiomerically pure R and S stereoisomers; other mixtures of the R and S stereoisomers; and pharmaceutically acceptable salts thereof.

The term "alkyl" is used herein to refer to both straight- and branched-chain saturated aliphatic hydrocarbon groups having about 1 to about 8 carbon atoms, and preferably about 1 to about 6 carbon atoms. The term "alkenyl" is used herein to refer to both straight- and branched-chain alkyl groups having one or more carbon-carbon double bonds and containing about 2 to about 8 carbon atoms. Preferably, the term alkenyl refers to an alkyl group having 1 or 2 carbon-carbon double bonds and having 2 to about 6 carbon atoms. The term "alkynyl" is used herein to refer to both straight- and branched-chain alkyl groups having one or more carbon-carbon triple bond and having 2 to about 8 carbon atoms. Preferably, the term alkynyl refers to an alkyl group having 1 or 2 carbon-carbon triple bonds and having 2 to about 6 carbon atoms.

The terms "substituted alkyl", "substituted alkenyl", and "substituted alkynyl" refer to alkyl, alkenyl, and alkynyl groups, respectively, having one or more substituents including, without limitation, halogen, CN, OH, $NO_2$, amino, aryl, heterocyclic, aryl, alkoxy, aryloxy, alkyloxy, alkylcarbonyl, alkylcarboxy, amino, and arylthio, which groups can be optionally substituted.

The term "acyl" as used herein refers to a carbonyl substituent, i.e., a C(O)(R) group where R is a straight- or branched-chain saturated aliphatic hydrocarbon group including, without limitation, alkyl, alkenyl, and alkynyl groups. Preferably, the R groups have 1 to about 8 carbon atoms, and more preferably 1 to about 6 carbon atoms. The term "substituted acyl" refers to an acyl group which is substituted with 1 or more groups including halogen, CN, OH, and $NO_2$.

The term "aryl" as used herein refers to an aromatic system which can include a single ring or multiple aromatic rings fused or linked together where at least one part of the fused or linked rings forms the conjugated aromatic system. The aryl groups include, but are not limited to, phenyl, naphthyl, biphenyl, anthryl, tetrahydronaphthyl, phenanthryl, indene, benzonaphthyl, fluorenyl, and carbazolyl.

The term "substituted aryl" refers to an aryl group which is substituted with one or more substituents including halogen, CN, OH, $NO_2$, amino, alkyl, cycloalkyl, alkenyl, alkynyl, alkoxy, aryloxy, alkyloxy, alkylcarbonyl, alkylcarboxy, alkylamino, and arylthio, which groups can be optionally substituted. Preferably, a substituted aryl group is substituted with 1 to about 4 substituents.

The term "heterocyclic" as used herein refers to a stable 4- to 7-membered monocyclic or multicyclic heterocyclic ring which is saturated, partially unsaturated, or wholly unsaturated. The heterocyclic ring has in its backbone carbon atoms and one or more heteroatoms including nitrogen, oxygen, and sulfur atoms. Preferably, the heterocyclic ring has about 1 to about 4 heteroatoms in the backbone of the ring. When the heterocyclic ring contains nitrogen or sulfur atoms in the backbone of the ring, the nitrogen or sulfur atoms can be oxidized. The term "heterocyclic" also refers to multicyclic rings in which a heterocyclic ring is fused to an aryl ring. The heterocyclic ring can be attached to the aryl ring through a heteroatom or carbon atom provided the resultant heterocyclic ring structure is chemically stable.

A variety of heterocyclic groups are known in the art and include, without limitation, oxygen-containing rings, nitrogen-containing rings, sulfur-containing rings, mixed heteroatom-containing rings, fused heteroatom containing rings, and combinations thereof. Oxygen-containing rings include, but are not limited to, furyl, tetrahydrofuranyl, pyranyl, pyronyl, and dioxinyl rings. Nitrogen-containing rings include, without limitation, pyrrolyl, pyrazolyl, imidazolyl, triazolyl, pyridyl, piperidinyl, 2-oxopiperidinyl, pyridazinyl, pyrimidinyl, pyrazinyl, piperazinyl, azepinyl, triazinyl, pyrrolidinyl, and azepinyl rings. Sulfur-containing rings include, without limitation, thienyl and dithiolyl rings. Mixed heteroatom containing rings include, but are not limited to, oxathiolyl, oxazolyl, thiazolyl, oxadiazolyl, oxatriazolyl, dioxazolyl, oxathiazolyl, oxathiolyl, oxazinyl, oxathiazinyl, morpholinyl, thiamorpholinyl, thiamorpholinyl sulfoxide, oxepinyl, thiepinyl, and diazepinyl rings. Fused heteroatom-containing rings include, but are not limited to, benzofuranyl, thionapthene, indolyl, benazazolyl, purindinyl, pyranopyrrolyl, isoindazolyl, indoxazinyl, benzoxazolyl, anthranilyl, benzopyranyl, quinolinyl, isoquinolinyl, benzodiazonyl, napthylridinyl, benzothienyl, pyridopyridinyl, benzoxazinyl, xanthenyl, acridinyl, and purinyl rings.

The term "substituted heterocyclic" as used herein refers to a heterocyclic group having one or more substituent including halogen, CN, OH, $NO_2$, amino, alkyl, cycloalkyl, alkenyl, alkynyl, alkoxy, aryloxy, alkyloxy, alkylcarbonyl, alkylcarboxy, alkylamino, and arylthio, which groups can be optionally substituted. Preferably, a substituted heterocyclic group is substituted with 1 to 4 substituents.

The term "aroyl" as used herein refers to a carbonyl substituent bound to a phenyl or heterocyclic group. Preferably, the aroyl heterocyclic groups include 2-pyridinyl, 3-pyridinyl, 2-furanyl, 3-furanyl, 3-thiophenyl, 2-pyrimidinyl, and 4-pyrimidinyl groups. The term "substituted aroyl" refers to an aroyl group which is substituted with one or more groups including, without limitation, halogen, CN, OH, and $NO_2$.

The term "thioalkyl" as used herein is used interchangeably with the term "thioalkoxy", with both referring to an S(alkyl) group, where the point of attachment is through the sulfur-atom and the alkyl group can be optionally substituted.

The term "arylthio" as used herein refers to the S(aryl) group, where the point of attachment is through the sulfur-atom and the aryl group can be optionally substituted.

The term "alkoxy" as used herein refers to the O(alkyl) group, where the point of attachment is through the oxygen-atom and the alkyl group is optionally substituted. The term "aryloxy" as used herein refers to the O(aryl) group, where the point of attachment is through the oxygen-atom and the aryl group is optionally substituted.

The term "alkylcarbonyl" as used herein refers to the C(O)(alkyl) group, where the point of attachment is through the carbon-atom of the carbonyl moiety and the alkyl group is optionally substituted.

The term "alkylcarboxy" as used herein refers to the C(O)O(alkyl) group, where the point of attachment is through the carbon-atom of the carboxy moiety and the alkyl group is optionally substituted.

The term "aminoalkyl" as used herein refers to both secondary and tertiary amines where the point of attachment is through the nitrogen-atom and the alkyl groups are optionally substituted. The alkyl groups can be the same or different.

The term "halogen" as used herein refers to Cl, Br, F, or I groups.

The compounds of formula I and II encompass tautomeric forms of the structures provided herein characterized by the bioactivity of the drawn structures. Further, the compounds of formula I and II can be used in the form of salts derived from pharmaceutically or physiologically acceptable acids, bases, alkali metals and alkaline earth metals.

Physiologically acceptable acids include those derived from inorganic and organic acids. A number of inorganic acids are known in the art and include hydrochloric, hydrobromic, hydroiodic, sulfuric, nitric, and phosphoric acids, among others. Similarly, a variety of organic acids are known in the art and include, without limitation, formic, acetic, propionic, oxalic, succinic, glycolic, glucuronic, maleic, furoic, fumaric, citric, glutamic, benzoic, anthranilic, salicylic, phenylacetic, mandelic, embonic, methanesulfonic, ethanesulfonic, panthenoic, benzenesulfonic, stearic, sulfanilic, alginic, and galacturonic acids, among others.

Physiologically acceptable bases include those derived from inorganic and organic bases. A number of inorganic bases are known in the art and include aluminum, calcium, lithium, magnesium, potassium, sodium, and zinc sulfate or phosphate compounds, among others. A number of organic bases are known in the art and include, without limitation, N,N,-dibenzylethylenediamine, chloroprocaine, choline, diethanolamine, ethylenediamine, meglumine, and procaine, among others. Physiologically acceptable alkali salts and alkaline earth metal salts can include, without limitation, sodium, potassium, calcium and magnesium salts in the form of esters, and carbamates. Other conventional "prodrug" forms can also be utilized which, when delivered in such form, convert to the active moiety in vivo.

The compounds of formula I and formula II can be prepared following the Schemes illustrated below.

Scheme 1

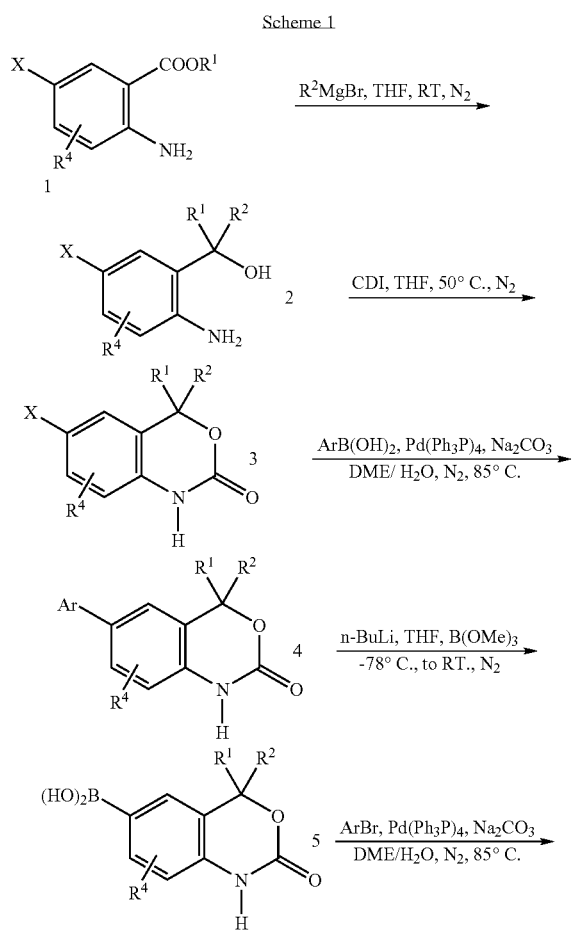

-continued

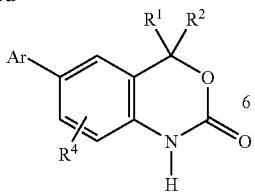

As demonstrated in Scheme I, the compounds of formulae I and II are generally prepared by employing the suitable coupling reaction as a final step. An appropriately substituted ortho-amino benzoic acid or its derivatives such as ethyl ester (X=Br, I, Cl, or a latent coupling precursor such as alkoxy group which can be converted into a OTf group suitable in the coupling reaction) was treated with a suitable organo metallic reagent, e.g., Grignard reagent, in appropriate nonprotic solvents which include, but are not limited to, tetrahydrofuran (THF) or ether to give ortho-amino carbinol 2 under an inert atmosphere such as argon or nitrogen at −78° C. to room temperature. Ring closure of carbinol 2 to yield benzoxazin-2-one 3 is commonly effected by a condensing agent such as carbonyldiimidazole, phosgene, dimethylcarbonate, or diethylcarbonate in a suitable nonprotic solvent such as THF at temperatures ranging from room temperature to 65° C. The arylation of benzoxazin-2-one 3 to yield 4 can be effected by various coupling reactions including Suzuki, Stille reactions. These reactions are commonly performed in the presence of transition metallic catalyst, e.g., palladium or nickel complex often with phosphino ligands, e.g., $Ph_3P$, dppf, dppe or palladium acetate. Under this catalytic condition, an appropriately substituted nucleophilic reagent, e.g., aryl boronic acid, arylstannane, or aryl zinc compound, is coupled with benzoxazinone 3 to give 4. If a base is needed in the reaction, the commonly used bases include, but are not limited to, sodium bicarbonate, sodium carbonate, potassium phosphate, barium carbonate, or potassium acetate. The most commonly used solvents in these reactions include benzene, dimethylformamide (DMF), isopropanol, ethanol, dimethoxyethane (DME), ether, acetone, or a mixture of above solvents and water. The coupling reaction is generally executed under an inert atmosphere such as nitrogen or argon at temperatures ranging from room temperature to 95° C.

Benzoxazinone 3 can be converted into a nucleophile such as boronic acid which can be coupled with an appropriate electrophile, e.g., aryl bromide or aryl iodide, to yield 4 employing the coupling reaction condition as described above. The transformation of 3 into 5 can be effected by treating 3 with an organometallic reagent, e.g., n-BuLi, in a nonprotic solvent such as THF or ether followed by quenching the reaction solution with a suitable electrophile, such as trimethyl borate, triisopropyl borate, or zinc chloride at temperatures ranging from −78° C. to room temperature under an inert atmosphere such as argon or nitrogen.

Scheme 1a

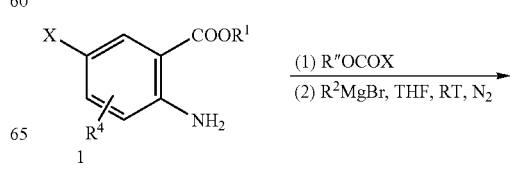

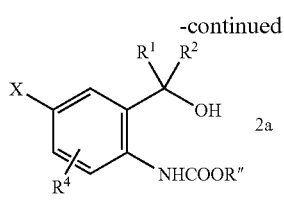

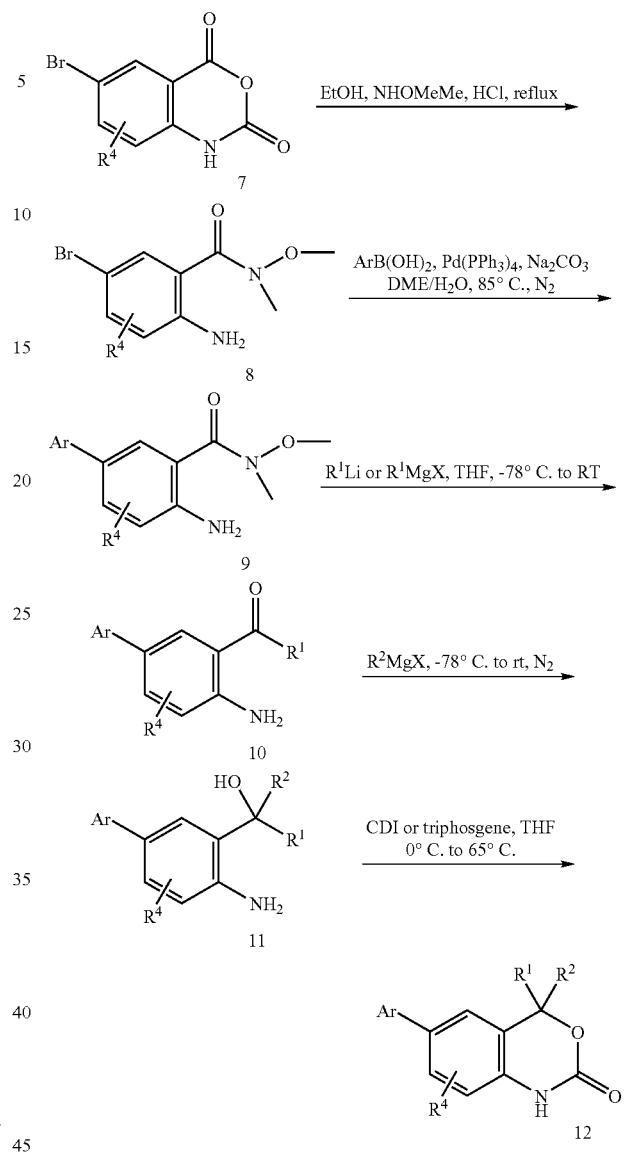

Scheme 1a illustrates an alternative approach leading to the benzoxazinone 3. Thus, an appropriate aniline 1 is protected with a suitable alkoxy carbonyl protective group including, but not limited to, allenoxy carbonyl, t-butoxy carbonyl, benzoxy carbonyl, ethoxy carbonyl, or methoxy carbonyl in a suitable solvent such as THF, acetonitrile, with or without presence of a base either as a catalyst or as an acid scavenger. The protected aniline is then treated with a suitable organometallic reagent such as an organolithium agent or Grignard reagent in the same fashion as to prepare compound 2 to give the carbinol 6. The treatment of 2a with a suitable base such as potassium t-butoxide, n-butyl lithium, potassium hydroxide in an appropriate solvent such as toluene, THF, alcohol under an inert atmosphere such as nitrogen or argon at temperatures ranging from room temperature to the boiling point of the relevant solvent to afford benzoxazinone 3.

Scheme II describes the procedures to prepare benzoxazinones bearing two different substituents at position-4. The Weinreb amide 8 can be prepared from an appropriately substituted isatoic anhydride 7 when treated with N—,O—dimethylhydroxyl-amine hydrochloride salt in a protic solvent such as ethanol, isopropanol at reflux under an inert atmosphere such as argon or nitrogen. Coupling of amide 8 with an aryl electrophile such as aryl boronic acid or arylstannane to give 9 can be effected by employing a typical coupling reaction such as Suzuki, Stille coupling procedure in a similar fashion as described for the preparation of benzoxazinones 4. Treatment of Weinreb amide 9 with organometallic compounds, e.g., alkyllithium, alkynyllithium, aryllithium, or their Grignard counterpart in a nonprotic solvent such as THF or ether under an inert atmosphere such as argon or nitrogen at −78° C. to room temperature affords amino ketone 10. Conversion of ketone 10 to carbinol 11 can be effected by treatment of 10 with an organometallic reagent such as alkyl, alkynyl, or aryl Grignard compound in a nonprotic solvent such as THF or ether under an inert atmosphere such as argon or nitrogen at −78° C. to room temperature. Conversion of ketone 10 to carbinol 11 can also be effected by reduction of ketone group of 10 to the carbinol moiety of 11 using an appropriate reducing reagent such as lithium aluminum hydride, sodium borohydride in a suitable solvent such as THF, ether, or anhydrous alcohol under an inert atmosphere in the temperature range from 0° C. to the boiling point of the solvent. Ring closure of carbinol 11 to produce the compounds of this invention can be accomplished with condensing agents such as carbonyldiimidazole, phosgene, dimethylcarbonate, or diethylcarbonate in a suitable nonprotic solvent such as THF at temperatures ranging from room temperature to 65° C.

Alternatively, ortho-amino ketone 10 can be prepared by treatment of ortho-amino benzonitrile 14 with an organometallic compound such as organolithium reagent or Grignard reagent in a suitable solvent such as THF or ether under an inert atmosphere such as argon or nitrogen at temperatures ranging from −78° C. to room temperature as illustrated in Scheme III. Benzonitrile 14 can be readily prepared from an appropriately substituted benzonitrile such as bromobenzonitrile 13 using a suitable coupling reaction such as Stille or Suzuki protocol carried out in a similar fashion as described for the preparation of the Weinreb amide 9.

Scheme III

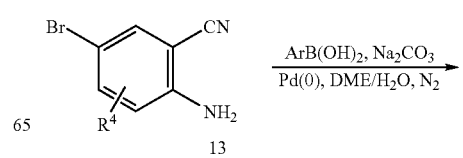

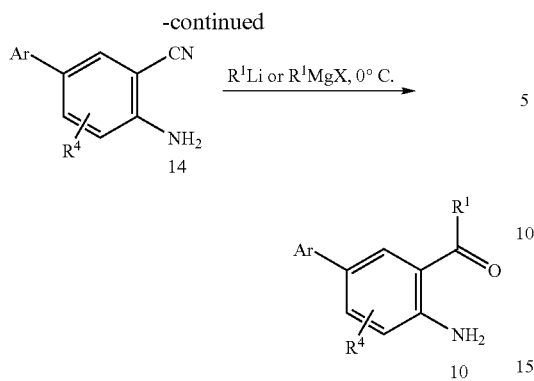

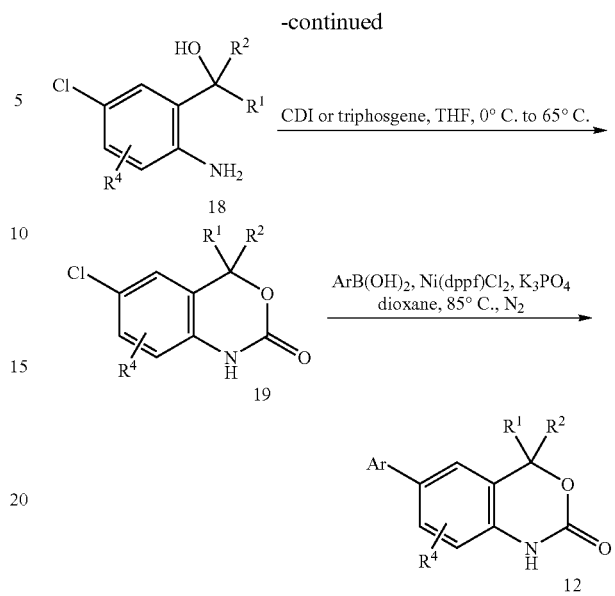

Scheme IV depicts an approach to prepare benzoxazinones with a low perfluoroalkyl substituent at position-4, e.g., $R^1$ is trifluoromethyl group. An appropriately substituted chloroaniline 15 was protected with a suitable protective group such as pivaloyl chloride or di-tert-butyl pyrocarbonate to give protected aniline 16 in a suitable solvent such as acetonitrile, acetone, THF, methylene chloride, or a mixture of solvent such as methylene chloride and water under an inert atmosphere such as argon or nitrogen at temperatures ranging from 0° C. to 70° C. A suitable base such as sodium carbonate, sodium bicarbonate, or potassium carbonate can be needed when the reaction produces an acid as a side-product such as hydrochloride. Treatment of 16 with an appropriate alkyllithium such as n-butyllithium or s-butyllithium followed by reaction with a low perfluorocarboxy derivatives, e.g., trifluoroacetyl chloride, 1-(trifluoroacetyl)-imidazole, or ethyl trifluoroacetate in a nonprotic solvent such as ether or THF under an inert atmosphere such as argon or nitrogen at −78° C. to ambient temperature gives the protective ortho-amino ketones. Subsequent removal of the protecting group can be effected by reaction of protected amino ketones with a suitable acid such as trifluoroacetate (TFA), 3N aqueous hydrochloride solution in a suitable solvent such as methylene chloride or water at 0° C. to boiling point of the solvent to afford ortho-amino ketone 17.

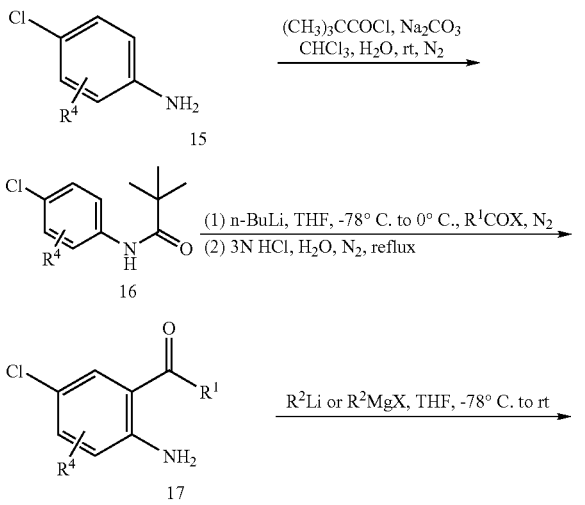

The preparation of 6-chlorobenzoxazinone 19 from 17 can be accomplished in the same fashion as described for the synthesis of benzoxazinone 12 from ketone 10. Coupling of 19 with an aryl group to yield 12 can be effected by a nickel complex catalyzed coupling reaction. The palladium catalysts proved not to be an efficient catalyst in this coupling process. The coupling reaction of 19 with an appropriate aryl boronic acid can be accomplished in the presence of a suitable base such as potassium phosphate and a catalyst of nickel (0 or II) complex, e.g. a nickel complex of 1,2-bis(diphenylphosphino)ethane, 1,1'-bis(diphenylphosphino)ferrocene, or triphenylphosphine. The most commonly used solvents in the reaction include dioxane or THF. The coupling reaction is generally executed under an inert atmosphere such as nitrogen or argon at temperatures ranging from ambient temperature to 95° C.

As described in Scheme V, the conversion of benzoxazin-2-one 3 or 12 into benzoxazin-2-thione 20 or 21 can be accomplished by treatment of 3 or 12 with a suitable sulfur reagent such as Lawesson's reagent in a nonprotic solvent such as o-xylene, chlorobenzene, or toluene under an inert atmosphere such as argon or nitrogen at reflux.

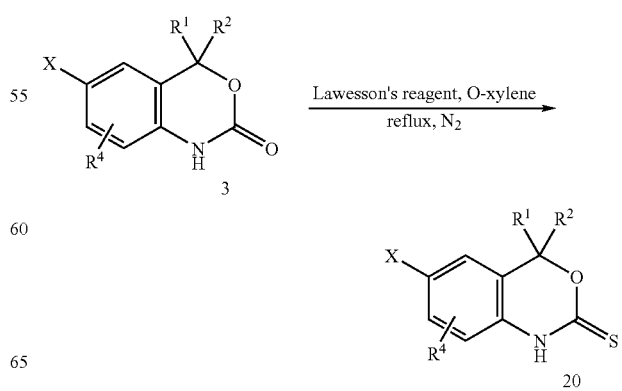

-continued

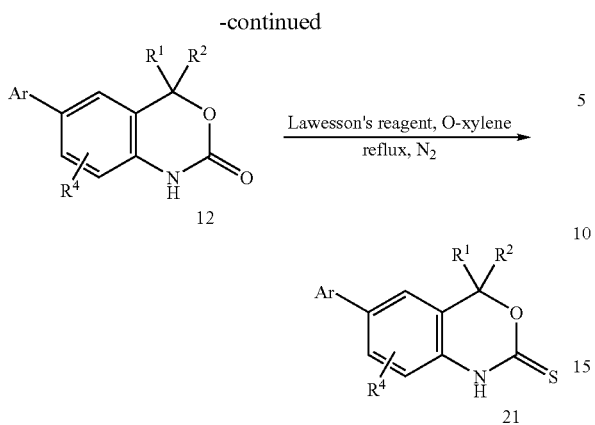

Schemes VI and VII describe the synthesis of other benzoxazinone bioisosteres. Using a similar procedure reported by Kondo et al. (Kondo, et al. J. Med. Chem. 33(7): 2012-2015 (1990)) compound 22 can be formed by treatment of amino carbinol 11 with an appropriate ketene-S, S-acetals (at least one of $R^7$ or $R^8$ is an electron withdrawing group) in a suitable solvent such as toluene or anhydrous ethanol under an inert atmosphere such as nitrogen or argon at reflux. In a similar fashion, compound 23 can be formed by reaction of amino carbinol 11 with an appropriate imino-S, S-acetals or imino-acetals ($R^6$ is an electron withdrawing group) employing a procedure similar to that of Evers, et al. (I. Prakt. Chem. 333(5): 699-710 (1991)) or Haake et al. (Synthesis-Stuttgart 9: 753-758 (1991)) in a suitable solvent such as ethanol under an inert atmosphere such as argon or nitrogen at reflux. Other procedures (e.g. Wrobel et al. J. Med. Chem. 32: 2493(1989)) potentially leading to compounds 22 or 23 from 20 or 21 are illustrated in Scheme VIIa. Thus, compound 20 or 21 is alkylated with an appropriate alkylating agent such as the Meerwein reagent in a suitable solvent such as methylene chloride. This is then followed by a nucleophilic replacement of an appropriate nucleophile such as carbon anion or an amine base to give compounds 22 or 23, which can produce either tautomeric form of compounds 22 or 23.

Scheme VI

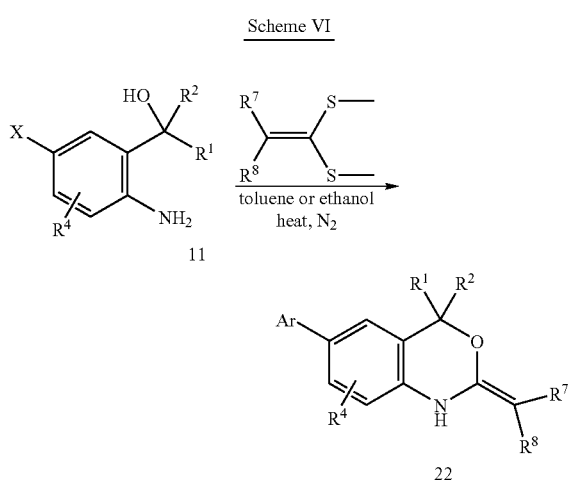

-continued
Scheme VII

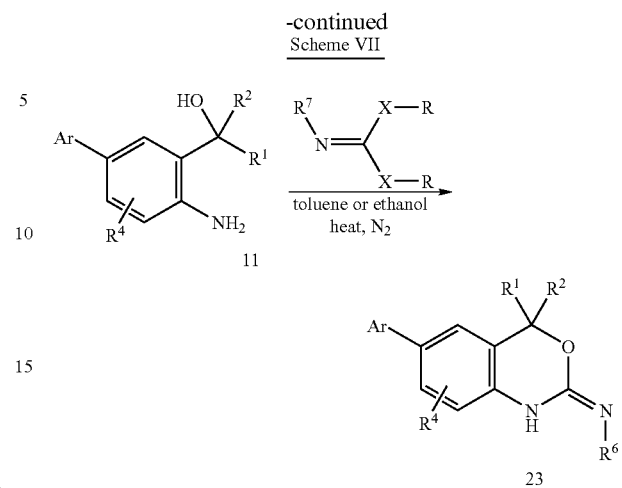

Scheme VIIa

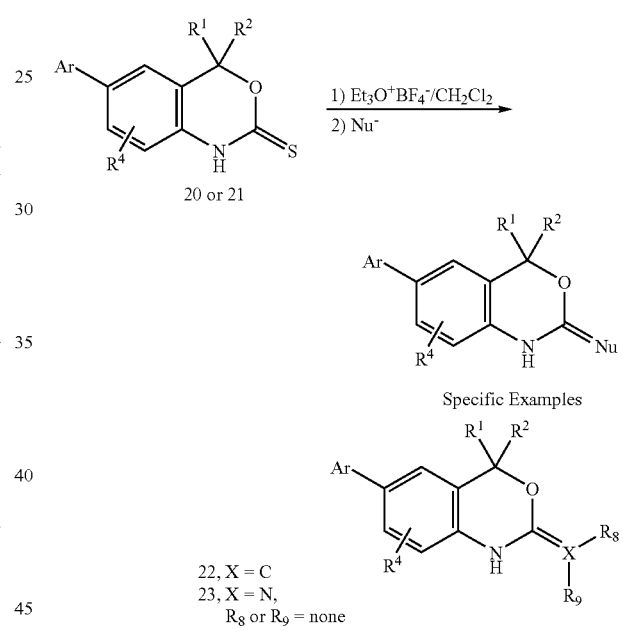

As illustrated in Scheme VIII, the compound 21 can be further derivatized at position-1 via numerous approaches leading to a variety of the novel cyclothiocarbamate derivatives including 1-alkyl, substituted 1-alkyl, 1-carbonyl, substituted 1-carbonyl, 1-carboxy, substituted 1-carboxy derivatives. For example, alkyl or substituted alkyl derivatives 24 can be formed by treatment of thiocarbamate 12 or 6 with a suitable base such as sodium hydride in suitable solvent such as DMF under an inert atmosphere, such as argon or nitrogen, followed by addition of an appropriate electrophile such as alkyl or substituted alkyl bromide, iodide, or triflate. Such a transformation of 21 at position-1 can also be effected using a biphasic condition as indicated in Scheme VIII in which alkylation is executed using a biphasic catalyst such as tributylammonium bromide in a suitable solvent such as acetonitrile. A further example of such a modification includes, but is not limited to, heating 21 with triethyl orthoformate to afford 1-substituted derivatives 24 (Scheme VIII).

The acylation or carboxylation of the compound 21 at position-1 to give compound 25 can be readily effected by treatment of 12 or 6 with a suitable acylating or carboxylating reagent such as di-t-butyl dicarbonate in the presence of a suitable basic catalyst such as dimethylaminophenol (DMAP) in a suitable solvent such as acetonitrile under an inert atmosphere such as argon or nitrogen. The amination of position-1 of compound 21 to give compound 26 can be furnished using a suitable aminating reagent such as chloroamine in the presence of a suitable base such as sodium hydride in a suitable solvent such as THF or diethyl ether following the literature procedure (Metlesics et al. J. Org. Chem. 30: 1311(1965)).

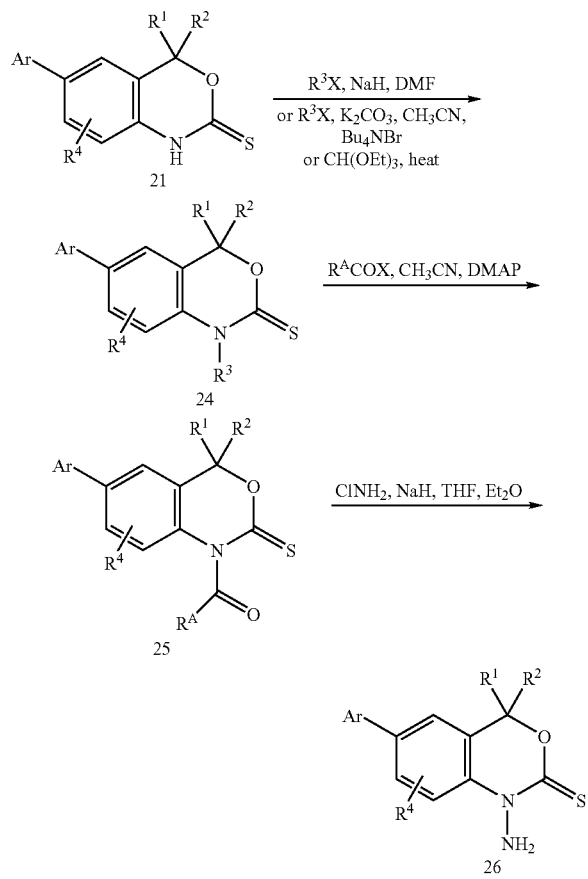

II. Formulations of the Invention

This invention includes pharmaceutical compositions comprising one or more compounds of this invention and a pharmaceutically acceptable carrier or excipient. The invention also includes methods of treatment which comprise administering to a mammal a pharmaceutically effective amount of one or more compounds as described above as modulators (i.e., agonists and/or antagonists) of the progesterone receptor.

The compounds of formula I and formula II as described herein can be formulated in any form suitable for the desired route of delivery using a pharmaceutically effective amount of one or more of the compounds of formula I or formula II. For example, the compositions of the invention can be delivered by a route such as oral, dermal, transdermal, intrabronchial, intranasal, intravenous, intramuscular, subcutaneous, parenteral, intraperitoneal, intranasal, vaginal, rectal, sublingual, intracranial, epidural, intratracheal, or by sustained release. Preferably, delivery is oral.

The effective dosage of active ingredient employed may vary depending on the particular compound employed, the mode of administration and the severity of the condition being treated, and any other active ingredient used in the formulation. However, in general, satisfactory results are obtained when the compounds of the invention are administered at a daily dosage of from about 0.5 to about 500 mg/kg of animal body weight, preferably given in divided doses two to four times a day, or in a sustained release form. For most large mammals, the total daily dosage is from about 1 to 100 mg, preferably from about 2 to 80 mg. Other suitable doses can be in the range of 5 to 50 mg or 10 to 25 mg. Advantageously, particularly potent PR modulators (e.g., those of formula II) may be useful at the lower end of the dosage ranges provided herein. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses (e.g., in divided doses 2 to 4 times a day) may be administered daily or the dose may be proportionally reduced as indicated by the exigencies of the therapeutic situation. Alternatively, a single dose can be delivered. Preferably, the delivery can be on a daily, weekly, or monthly basis, and more preferably on a daily delivery. Daily dosages can be lowered or raised based on the periodic delivery.

The compounds of formula I and II may also be formulated with and/or delivered in combination with, other active ingredients including, e.g., other progesterone receptor modulators, estrogens, estrogen receptor modulators, and the like. For example, when used for treatment of skin disorders, it may be desirable to include skin conditioning agents in the formulation of a compound of formula I and/or II, or to deliver such agents in a combination regimen such as described below. Skin conditioning agents can include any reagent which provides a conditioning effect to the skin and/or does not clog the pores of the skin. A number of skin conditioning agents are known in the art and include, without limitation, skin conditioning agents that can be applied to the skin, including water-based lotions, creams, pastes, gels, ointments or foams.

The compound(s) of formula I and formula II can be combined with one or more pharmaceutically acceptable carriers or excipients including, without limitation, solid and liquid carriers which are compatible with the compositions of the present invention. Solid carriers include, without limitation, starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Carriers can also include solvents, adjuvants, syrups, elixirs, diluents, binders, lubricants, surfactants, granulating agents, disintegrating agents, emollients, and combinations thereof.

Adjuvants can include, without limitation, flavoring agents, coloring agents, preservatives, and supplemental antioxidants, which can include vitamin E, ascorbic acid, butylated hydroxytoluene (BHT) and butylated hydroxyanisole (BHA).

Elixers and/syrups can be prepared from acceptable sweeteners such as sugar, saccharine or a biological sweetener, a flavoring agent, and/or solvent. In one embodiment, a syrup can contain about 10 to about 50% of a sugar carrier. In another embodiment, the elixir can contain about 20 to about 50% of an ethanol carrier.

Diluents can include materials in which the compound can be dispersed, dissolved, or incorporated. Preferably, the diluents include water, lower monovalent alcohols, and low molecular weight glycols and polyols, including propylene glycol, diethylene glycol, polyethylene glycol, polypropylene glycol, glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers, oils such as corn, peanut and sesame oils, dimethylsulfoxide (DMSO), dimethylformamide (DMF), and combinations thereof. Preferably, the diluent is water.

Binders can include, without limitation, cellulose, methylcellulose, hydroxymethylcellulose, polypropylpyrrolidone, polyvinylpyrrolidone, gelatin, gum arabic, polyethylene glycol, starch, sugars such as sucrose, kaolin, and lactose, among others.

Lubricants can include magnesium stearate, light anhydrous silicic acid, talc and sodium lauryl sulfate, among others.

Granulating agents can include, without limitation, silicon dioxide, microcrystalline cellulose, starch, calcium carbonate, pectin, and crospovidone, polyplasdone, among others.

Disintegrating agents can include starch, carboxymethylcellulose, hydroxypropylstarch, substituted hydroxypropylcellulose, sodium bicarbonate, calcium phosphate, and calcium citrate, among others Emollients can include, without limitation, stearyl alcohol, mink oil, cetyl alcohol, oleyl alcohol, isopropyl laurate, polyethylene glycol, olive oil, petroleum jelly, palmitic acid, oleic acid, and myristyl myristate.

For example, the compounds may be formulated for administration orally in such forms as tablets, capsules, microcapsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like. The preferred pharmaceutical compositions from the standpoint of ease of preparation and administration are solid compositions, particularly tablets and hard-filled or liquid-filled capsules.

The active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid, polyethylene glycols and mixtures thereof in oils. Under ordinary conditions of storage and use, these preparations contain a preservative to prevent the growth of microorganisms. Typically, such sterile injectable solutions or suspensions contain from about 0.05 to 5% suspending agent in an isotonic medium. Such pharmaceutical preparations may contain, for example, from about 25 to about 90% of the active ingredient in combination with the carrier, more usually between about 5% and 60% by weight.

In another embodiment, the compounds are delivered intravenously, intramuscularly, subcutaneously, parenterally and intraperitoneally in the form of sterile injectable solutions, suspensions, dispersions, and powders which are fluid to the extent that easy syringe ability exits. Such injectable compositions are sterile, stable under conditions of manufacture and storage, and free of the contaminating action of microorganisms such as bacteria and fungi.

The carrier can be a solvent or dispersion medium containing, for example, water, ethanol (e.g., glycerol, propylene glycol and liquid polyethylene glycol), oils, and mixtures thereof. Preferably the liquid carrier is water. In one embodiment, the oil is vegetable oil. Optionally, the liquid carrier contains a suspending agent. In another embodiment, the liquid carrier is an isotonic medium and contains 0.05 to about 5% suspending agent.

In a further embodiment, the compounds are delivered rectally in the form of a conventional suppository.

In another embodiment, the compounds are delivered vaginally in the form of a conventional suppository, cream, gel, ring, or coated intrauterine device (IUD).

In yet another embodiment, the compositions are delivered intranasally or intrabronchially in the form of an aerosol.

In a further embodiment, the compounds are delivered transdermally or by sustained release through the use of a transdermal patch containing the composition and an optional carrier that is inert to the compound, is nontoxic to the skin, and allows for delivery of the compound for systemic absorption into the blood stream. Such a carrier can be a cream, ointment, paste, gel, or occlusive device. The creams and ointments can be viscous liquid or semisolid emulsions. Pastes include absorptive powders dispersed in petroleum or hydrophilic petroleum. Further, a variety of occlusive devices can be utilized to release the active reagents into the blood stream and include semi-permeable membranes covering a reservoir contain the active reagents, or a matrix containing the reactive reagents.

The use of sustained delivery devices can be desirable, in order to avoid the necessity for the patient to take medications on a daily basis. The term "sustained delivery" is used herein to refer to delaying the release of an active agent, i.e., a compound of the invention, until after placement in a delivery environment, followed by a sustained release of the agent at a later time. A number of sustained delivery devices are known in the art and include hydrogels (U.S. Pat. Nos. 5,266,325; 4,959,217; 5,292,515), osmotic pumps (U.S. Pat. Nos. 4,295,987 and 5,273,752 and European Patent No. 314,206, among others); hydrophobic membrane materials, such as ethylenemethacrylate (EMA) and ethylenevinylacetate (EVA); bioresorbable polymer systems (International Patent Publication No. WO 98/44964 and U.S. Pat. Nos. 5,756,127 and 5,854,388); and other bioresorbable implant devices composed of, for example, polyesters, polyanhydrides, or lactic acid/glycolic acid copolymers (U.S. Pat. No. 5,817,343). For use in such sustained delivery devices, the compounds of the invention can be formulated as described herein. See, U.S. Pat. Nos. 3,845,770; 3,916,899; 3,536,809; 3,598,123; and 4,008,719.

In yet another embodiment, the compounds are topically delivered using a topical vehicle including creams, pastes, gels, ointments, lotions, liquids, solutions, suspensions, or foams or can be alone delivered prior or subsequent to the topical vehicle. Topical compositions can be applied to the area of the body which is afflicted with the skin disorder and includes the face, scalp, legs, arms, torso, or armpits. Preferably, the topical vehicles are anti-comedogenic.

III. Therapeutic Regimens

In one embodiment, the present invention provides dosing regimens utilizing the compound(s) of formula I and/or formula II with a physiologically acceptable carrier for use in treatment of skin disorders.

In another embodiment, the progesterone receptor modulators of formula II, used alone or in combination, can be utilized in methods of contraception, in the treatment of fibroids, endometriosis, breast, uterine, ovarian and prostate cancer, hormone replacement therapy, skin disorders, and the treatment and/or prevention of benign and malignant neoplastic disease. Specific uses of the compounds and pharmaceutical compositions of invention include the treatment and/or prevention of uterine myometrial fibroids, endometriosis, benign prostatic hypertrophy; carcinomas and adenocarcinomas of the endometrium, ovary, breast, colon, prostate, pituitary, meningioma and other hormone-dependent tumors. Additional uses of the present progesterone receptor modulators include the synchronization of the estrus in livestock.

The compositions of the invention can be delivered by any suitable route, including, e.g., oral, dermal, transdermal, intrabronchial, intranasal, intravenous, intramuscular, subcutaneous, parenteral, intraperitoneal, intranasal, vaginal, rectal, sublingual, intracranial, epidural, intratracheal, or by sustained release. Preferably, delivery is oral.

The regimens of the invention can include the continuous delivery of the compounds of the invention. In another embodiment, the regimens can include the periodic discontinuation of delivery of a compound of formula I and/or formula II. Such periodic discontinuation can include delivery of a placebo during the period of time where the compounds of the invention are not delivered to the patient. Alternatively, no placebo or active agent is delivered to the patient when the compounds are not being delivered to the patient.

By the term "placebo" or "inactive agent" is meant a reagent having pharmacological properties that are not relevant to the condition being treated, i.e., does not contain an active agent. Typical placebos include sugar as the primary constituent.

By the term "active agent" is meant any reagent which assists in treating a hormone-related condition.

The method of the present invention can be carried out over a cycle of 21 or more days, preferably 21 or more consecutive days, more preferably 21, 28, 30, or 31 days, and most preferably 21 or 28 days. One of skill in the art would readily be able to select and adjust the appropriate period of delivery.

The terminal portion of a cycle can be the last 1 to about 10 days of the cycle, and preferably the last 7 days of the cycle. In one embodiment, the terminal portion of the 28-day cycle can include the last 7 days of the cycle, i.e., days 22 to 28 of the 28-day cycle. The terminal portion of a cycle can include the delivery of an agent other than the compositions of the invention and is preferably a placebo. Alternatively, no agent or placebo is delivered during the terminal portion of the cycle.

The regimen can include delivering a daily dosage of a compound of formula I and/or formula II, which is incorporated into a single daily dosage unit. Delivery of a compound of formula I and/or formula II can be prior to, simultaneous with, or subsequent to the delivery of other reagents that can be used according to the present invention.

The regimen can further include alternating delivery of a compound of formula I and/or formula II alone, other reagent(s) that can be used according to the present invention, and a combination of the compound and the other reagent(s).

In one embodiment, a single daily dosage of a compound of formula I and/or formula II can be delivered for the entire 21-day, 28-day, 30-day, or 31-day cycle. Alternatively, a single daily dosage of the compound of formula I and/or formula II can be delivered for the first 21 days of a 28-day, 30-day, or 31-day cycle. A single daily dosage of a compound of formula I and/or formula II can also be delivered for the first 24 days of a 28-day, 30-day, or 31-day cycle.

The regimen can further include alternating delivery of a compounds of formula I and/or formula II alone, an estrogen alone, and a combination of the compound and the estrogen. The regimen can also include the delivery of another reagent prior to, in conjunction with, or subsequent to a compound of formula I and/or formula II and the estrogen.

In one embodiment, a single combined daily dosage of a compound of formula I and/or formula II and an estrogen can be delivered for the entire 21-day, 28-day, 30-day, or 31-day cycle. Alternatively, a single combined daily dosage of a compound of formula I and/or formula II and an estrogen can be delivered for the first 21 days of a 28-day, 30-day, or 31-day cycle. A single combined daily dosage of a compound of formula I and/or formula II and an estrogen can also be delivered for the first 24 days of a 28-day, 30-day, or 31-day cycle.

In a further embodiment, a daily dosage of a compound of formula I and/or formula II can be delivered by one route of delivery and a daily dosage of an estrogen can be delivered by a second route of delivery for the entire 21-day, 28-day, 30-day, or 31-day cycle. Alternatively, a daily dosage of a compound of formula I and/or formula II can be delivered by one route of delivery and a daily dosage of an estrogen can be delivered by a second route of delivery for the first 21 days of a 28-day, 30-day, or 31-day cycle. Further, a daily dosage of a compound of formula I and/or formula II can be delivered by one route of delivery and a daily dosage of an estrogen can be delivered by a second route of delivery for the first 24 days of a 28-day, 30-day, or 31-day cycle.

In another embodiment, a daily dose of a compound of formula I and/or formula II can be delivered, followed by a daily dose of an estrogen for the entire 21-day, 28-day, 30-day, or 31-day cycle. Alternatively, a daily dose of a compound of formula I and/or formula II can be delivered, followed by a daily dose of an estrogen for the first 21 days of a 28-day, 30-day, or 31-day cycle. Alternatively, a daily dosage of a compound of formula I and/or formula II can be delivered, followed by a daily dosage of an estrogen for the first 24 days of a 28-day, 30-day, or 31-day cycle.

In a further embodiment, a compound of formula I and/or formula II are delivered with an estrogen for the first 14 to 24 days of a 28-day cycle, followed by delivery of the estrogen alone for a period of 1 to 11 days beginning on any cycle day between day 14 and 24.

In another embodiment, a compound of formula I and/or formula II can be delivered for the initial 18 to 21 days of a 28-day cycle, followed by delivery of an estrogen alone for from 1 to 7 days.

In yet a further embodiment, a compound of formula I and/or formula II can be delivered alone over a 28 day cycle for the first 21 days, followed by delivery of an estrogen alone from day 22 to day 24.

The dosage regimens can be adjusted to provide the optimal therapeutic response. For example, several divided doses of each component can be delivered daily or the dose can be proportionally increased or reduced as indicated by the exigencies of the therapeutic situation. In the descriptions herein, reference to a daily dosage unit can also include divided units which are delivered over the course of each day of the cycle contemplated.

Optionally, when a compound of formulae I and/or II are used in the treatment of skin disorders, other conventional acne-reducing compounds are included in the compositions and/or regimens of the invention. Such acne-reducing compounds can assist in the reduction of redness and/or blemishes. A large number of acne-reducing compounds are known in the art and include carotenoid agents, vitamin B sources, zinc compounds, and combinations thereof See, U.S. Pat. No. 5,962,517.

Carotenoid agents can be included in the composition of the invention or can be alone delivered prior or subsequent to the compound or composition and include those carotenoids which exhibit antioxidant behavior. Preferably, the carotenoid agent includes beta-carotene, canthaxanthin, zeaxanthin, lycopen, lutein, crocetin, capsanthin, and vitamin A sources. The vitamin A sources can include vitamin A acetate or vitamin A palmitate. More preferably, the carotenoid agent is beta-carotene.

Vitamin B sources can also included in the composition of the invention or can be alone delivered prior or subsequent to the composition to assist or promote the formation of amino acids and collagen. Preferably, the vitamin B source is a $B_6$ source, which can include, without limitation, pyridoxine, pyridoxal, and pyridoxamine, and more preferably is pyridoxine.

Further, zinc compounds can be included in the composition of the present invention or can be alone delivered prior or subsequent to the composition. The zinc compound can include any zinc compound, preferably a zinc compound which promotes the reduction of inflammation, more preferably zinc ascorbic acid or zinc ascorbate, and most preferably zinc ascorbate.

Penetration enhancers, when used according to the method of the invention in treating hirsutism, can include any reagent that enhances the penetration of a compound through one or more layers of the skin and/or to the site of the skin disorder. A number of penetration enhancers are known in the art and include, but are not limited to, urea, proan-2-ol, polyoxyethylene ethers, terpenes, cis-fatty acids, including oleic acid and palmitoleic acid, acetone, laurocapram dimethyl sulfoxide, 2-pyrrolidone, oleyl alcohol, glyceryl-3-stearate, cholesterol, myristic acid isopropyl ester, propylene glycol, and combinations thereof.

When included in the compositions and/or regimens of the present invention, estrogens can include natural estrogens, synthetic estrogens, catechol estrogens, conjugated estrogens, and non-steroidal estrogens, among others, or pharmaceutically acceptable salts or esters thereof. In one embodiment, the estrogen is a natural estrogen including estrone, including the acetate, propionate, sulfate, and sulfate piperazine ester salts; estradiol, including the 3-benzoate, 17b-cypionate, 17-proprionate, d-propionate, hemisuccinate, 17-heptanotate, 17-undecanoate, and 17-valerate ester salts; or estriol. In another embodiment, the estrogen is a synthetic estrogen including ethinyl estradiol. In a further embodiment, the estrogen is a conjugated estrogen including conjugated equine estrogens and sodium estrone sulfate and is available in formulations for intravenous, intramuscular, and topical administration (Wyeth). In a further embodiment, the estrogen is a catechol estrogen including 2- or 4-hydroxyestrogens. In yet another embodiment, the nonsteroidal estrogen is diethylstilbestrol. See, Chapter 50 entitled "Hormones" in Remington's Pharmaceutical Sciences, 18$^{th}$ Ed., Mack Publishing Company, Easton, Penn., 1990. The desired estrogen may however be selected from a variety of products commercially available. One of skill in the art would readily be able to select the estrogen, as well as dosage, that achieves the desired effect. Preferably, the estrogen is present in the formulation at about 0.01 mg to about 1.0 mg.

Other reagents can be delivered in combination with the compositions of the present invention. Alternatively, such reagents can be alone administered prior or subsequent to the compositions of the invention. Such reagents can include drying agents including alcohols and benzoyl peroxides; vitamin C and D sources; amino acid reagents; enzyme activators; mineral oil; lanolin; propylene glycol; sodium lauryl sulfate; among others, and combinations thereof. The term "enzyme activator" is meant to describe a reagent which activates fat and glucose metabolism and thereby results in the prevention of future acne occurrences. Preferably, the enzyme activator is a transition metal complex, more preferably is a group 5 or 6 transition metal complex, and most preferably a vanadium or chromium complex. Further, oral reagents include antibiotics; anti-inflammatory agents; herbal extracts including burdock root, yellow dock, horsetail, dandelion root, licorice root, echinacea, kelp, cayenne, sassafras, and elder flowers; xanthan gum; cytokines, androgens, and antiprogestins. Antibiotics, can also be applied as in a topical vehicle.

IV. Pharmaceutical Kits

The present invention provides kits or packages of pharmaceutical formulations designed for use in the regimens described herein. These kits are preferably designed for daily oral delivery over 21-day, 28-day, 30-day, or 31-day cycles, among others, and more preferably for one oral delivery per day. When the compositions are to be delivered continuously, a package or kit can include the composition in each tablet. When the compositions are to be delivered with periodic discontinuation, a package or kit can include placebos on those days when the composition is not delivered.

The kits are also preferably organized to indicate a single oral formulation or combination of oral formulations to be taken on each day of the cycle, preferably including oral tablets to be taken on each of the days specified, and more preferably one oral tablet will contain each of the combined daily dosages indicated.

In one embodiment, a kit can include a single phase of a daily dosage of the compound of formula I or formula II over a 21-day, 28-day, 30-day, or 31-day cycle. Alternatively, a kit can include a single phase of a daily dosage of a compound of formula I and/or formula II over the first 21 days of a 28-day, 30-day, or 31-day cycle. A kit can also include a single phase of a daily dosage of a compound of formula I and/or formula II over the first 28 days of a 30-day or 31-day cycle.

In a further embodiment, a kit can include a single combined phase of a daily dosage of a compound of formula I and/or formula II and an estrogen over a 21-day, 28-day, 30-day, or 31-day cycle. Alternatively, a kit can include a single combined phase of a daily dosage of a compound of formula I and/or formula II and an estrogen over the first 21 days of a 28-day, 30-day, or 31-day cycle. A kit can also include a single combined phase of a daily dosage of a compound of formula I and/or formula II and an estrogen over the first 28 days of a 30-day or 31-day cycle.

In another embodiment, a 28-day kit can include a first phase of from 14 to 28 daily dosage units of a compound of formula I and/or formula II; a second phase of from 1 to 11 daily dosage units of an estrogen; and, optionally, a third phase of an orally and pharmaceutically acceptable placebo for the remaining days of the cycle.

In yet a further embodiment, a 28-day kit can include a first phase of from 14 to 21 daily dosage units of the compound of formula I and/or formula II; a second phase of from 1 to 11 daily dosage units of an estrogen; and, optionally, a third phase of an orally and pharmaceutically acceptable placebo for the remaining days of the cycle.

In another embodiment, a 28-day kit can include a first phase of from 18 to 21 daily dosage units of a compound of formula I and/or formula II; a second phase of from 1 to 7 daily dose units of an estrogen; and, optionally, an orally and pharmaceutically acceptable placebo for each of the remaining 0 to 9 days in the 28-day cycle.

In a preferred embodiment, a 28-day kit can include a first phase of 21 daily dosage units of a compound of formula I and/or formula II; a second phase of 3 daily dosage units for days 22 to 24 of an estrogen; and, optionally, a third phase of 4 daily units of an orally and pharmaceutically acceptable placebo for each of days 25 to 28.

Similarly, other kits of the type described above may be prepared in which a compound of formula I, formula II, or combinations thereof, are delivered in a regimen comprising active ingredients in addition to, or in place of an estrogen.

Preferably, the daily dosage of each pharmaceutically active component of the regimen remain fixed in each particular phase in which it is delivered. It is further preferable that the daily dose units described are to be delivered in the order described, with the first phase followed in order by the second and third phases. To help facilitate compliance with each regimen, it is also preferred that the kits contain the placebo described for the final days of the cycle.

A number of packages or kits are known in the art for the use in dispensing pharmaceutical agents for oral use. Preferably, the package has indicators for each day of the 28-day cycle, and more preferably is a labeled blister package, dial dispenser package, or bottle.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLE 1

1-Methyl-5-(2-thioxo-1,2-dihydrospiro[3,1-benzoxazine-4,1'-cyclobutan]-6-yl)-1H-pyrrole-2-carbonitrile A. tert-Butyl [2-(1-Hydroxycyclobutyl)phenyl]carbamate To phenyl-carbamic acid tert-butyl ester (2 g, 10.4 mmol) in ether (30 mL) at 0° C. was added t-BuLi (15 mL, 26 mmol, 1.7 M) and the reaction solution stirred for 3 hours prior to the addition of cyclobutanone (1.2 mL, 15.6 mmol). The reaction mixture was allowed to warm to room temperature. Upon completion by thin-layer chromatography (TLC), the reaction was poured into ice-cold saturated ammonium chloride (100 mL) and extracted with ethyl acetate (50 mL). The organics were dried over sodium sulfate, concentrated, and purified on a silica gel column (10% ethyl acetate/hexane) to give tert-butyl [2-(1-hydroxycyclobutyl)-phenyl]carbamate (0.86 g, 32%) as a white solid. $^1$H NMR (DMSO-$d_6$): δ 8.48 (s, 1H), 7.8 (d, 1H, J=7.92 Hz ), 7.35 (dd, 1H, J=7.7, 1.4 Hz), 7.25 (td, 1H, J=7.5, 1.6 Hz), 7.03 (td, 1H, J=7.5, 1.3 Hz), 2.51-2.49 (m, 2H), 2.43-2.39 (m, 2H), 2.28-2.25 (m, 2H), 1.45 (s, 9H). MS (ESI) m/z 190 ([M+H]$^+$); MS (ESI) m/z 188 ([M−H]$^-$);

B. Spiro[3,1-benzoxazine-4,1'-cyclobutan]-2(1H)-one

A solution of tert-butyl [2-(1-hydroxycyclobutyl)phenyl] carbamate (0.86 g, 3.3 mmol) in ethanol (30 mL) was stirred with potassium hydroxide (0.39 g, 6.9 mmol) at room temperature for 3 hours. The product was extracted with ethyl acetate (50 mL), dried with sodium sulfate, and concentrated to give spiro[3,1-benzoxazine-4,1'-cyclobutan]-2(1H)-one (0.36 g, 58%) as a white solid. $^1$H NMR (DMSO-$d_6$): δ 10.21 (s, 1H), 7.47 (dd, 1H, J=7.6, 1.2 Hz), 7.28 (td, 1H, J=7.6, 1.4 Hz), 7.08 (td, 1H, J=7.5, 1.2 Hz), 6.9 (dd, 1H, J=7.9, 0.9 Hz), 2.49-2.41 (m, 2H), 2.06-1.96 (m, 2H), 1.88-1.77 (m, 2H). MS (ESI) m/z 190 ([M+H]$^+$).

C. 6-Bromospiro[3,1-benzoxazine-4,1'-cyclobutan]-2 (1H)-one

To a solution of spiro[3,1-benzoxazine-4,1'-cyclobutan]-2(1H)-one (0.36 g, 1.9 mmol) and potassium acetate (0.56 g, 5.7 mmol) in acetic acid was added a solution of bromine (0.09 mL, 1.95 mmol) in acetic acid (2 mL) at room temperature. Upon completion by TLC of the reaction, the acetic acid was removed. The residue was treated with saturated sodium bicarbonate (100 mL) and the product extracted with ethyl acetate (50 mL). The organics were dried over magnesium sulfate and concentrated. Trituration of residue with ether gave 6-bromospiro[3,1-benzoxazine-4,1'-cyclobutan]-2(1H)-one (0.27 g, 52%) as a white solid. $^1$H NMR (DMSO-$d_6$): δ 10.37 (s, 1H), 7.65 (d, 1H, J=2.1 Hz), 7.47 (dd, 1H, J=8.5, 2.2 Hz) 6.86 (d, 1H, J=8.5 Hz), 2.52-2.47 (m, 2H), 2.04-1.98 (m, 2H), 1.87-1.80 (m, 2H). MS (ESI) m/z 268/270 ([M+H]$^+$); MS (ESI) m/z 266/268 ([M−H]$^-$).

D. 1-Methyl-5-(2-oxo-1,2-dihydrospiro [3,1-benzoxazine-4,1'-cyclobutan]-6-yl)-1H-pyrrole-2-carbonitrile To a solution of 1-methyl-1H-pyrrole-2-carbonitrile (0.84 g, 7.1 mmol) and triisopropylborate (1.8 mL, 7.8 mmol) in THF (15 mL) at 0° C. was added lithium diisopropylamide (4.6 mL, 9.2 mmol). The reaction was allowed to warm to room temperature. Upon completion by TLC, the reaction was added dropwise to a 65° C. solution of 6-bromospiro [3,1-benzoxazine-4,1'-cyclobutan]-2(1H)-one (0.38 g, 1.4 mmol), potassium carbonate (0.58 g, 4.2 mmol) dissolved in (5 mL water), and tetrakistriphenylphosphine palladium (0) (0.081 g, 0.07 mmol) in tetrahydrofuran (10 mL). Upon completion by TLC of the reaction the reaction mixture was poured into a saturated solution of ammonium chloride (100 mL), extracted with ethyl acetate (50 mL), dried with magnesium sulfate, and purified on a silica gel column (40% ethyl acetate/hexane) to give 1-methyl-5-(2-oxo-1,2-dihydrospiro[3,1-benzoxazine-4,1'-cyclobutan]-6-yl)-1H-pyrrole-2-carbonitrile (0.33 g, 79%) as a light red solid. $^1$H NMR (DMSO-$d_6$): δ 10.41 (s, 1H), 7.58 (d, 1H, J=2 Hz), 7.43 (dd, 1H, J=8.2, 1.8 Hz), 7.04 (d, 1H, J=4.0 Hz), 6.39 (d, 1H, J=8.2 Hz), 6.39 (d, 1H, J=4.0 Hz), 3.73 (s, 3H), 2.55-2.49 (m, 2H), 2.05-1.90 (m, 2H), 1.88-1.83 (m, 2H). MS (ESI) m/z 294 ([M+H]+); MS (ESI) m/z 292 ([M−H]−). High resolution mass spectrometry (HRMS): calcd for $C_{17}H_{15}N_3O_2$, 293.1164; found (ESI_FT), 294.12311.

A solution of 1-methyl-5-(2-oxo-1,2-dihydrospiro [3,1-benzoxazine-4,1'-cyclobutan]-6-yl)-1H-pyrrole-2-carbonitrile (0.33 g, 1.1 mmol) and Lawesson's Reagent (0.23 g, 0.55 mmol) in toluene (10 mL) was heated at 100° C. Upon completion by TLC, the reaction mixture was poured into saturated sodium carbonate (100 mL) and extracted with ethyl acetate (50 mL), dried over magnesium sulfate, and concentrated. Trituration of the residue with ether (20 mL) gave 1-methyl-5-(2-thioxo-1,2-dihydrospiro[3,1-benzoxazine-4,1'-cyclobutan]-6-yl)-1H-pyrrole-2-carbonitrile (0.17 g, 49%) as a tan solid. $^1$H NMR (DMSO-$d_6$): δ 12.35 (s, 1H), 7.64 (d, 1H, J=2.0 Hz), 7.51 (dd, 1H, J=8.2, 2.0 Hz), 7.15 (d, 1H, J=8.3 Hz), 7.05 (d, 1H, J=4.03 Hz), 6.43 (d, 1H, J=4.03 Hz), 3.73 (s, 3H), 2.59-2.53 (m, 2H), 2.09-2.02 (m, 2H), 1.93-1.85 (m, 2H). MS (ESI) m/z 310 ([M+H]+); MS (ESI) m/z 308 ([M−H]−); HRMS: calcd for $C_{17}H_{15}N_3OS$, 309.0936; found (ESI_FT), 310.10057.

EXAMPLE 2

5-(4,4-Diethyl-2-thioxo-1,4-dihydro-2H-3,1-benzoxazin-6-yl)-1-methyl-1H-pyrrole-2-carbonitrile A. 5-(4,4-Diethyl-2-oxo-1,4-dihydro-2H-3,1-benzoxazin-6-yl)-1-methyl-1H-pyrrole-2-carbonitrile To a solution of 1-methyl-1H-pyrrole-2-carbonitrile (4.1 g, 35 mmol) and triisopropylborate (8.9 mL, 38.5 mmol) in THF (80 mL) at 0° C. was added lithium diisopropylamide (22.8 mL, 45.5 mmol). The reaction mixture was allowed to warm to room temperature. Upon completion by TLC, the reaction was added dropwise to a 65° C. solution of 6-bromo-4,4-diethyl-1,4-dihydro-benzo[d][1,3]oxazin-2-one (2.0 g, 7.0 mmol), potassium carbonate (2.9 g, 21 mmol) dissolved in (25 mL water), and tetrakistriphenylphosphine palladium (0) (0.4 g, 0.35 mmol) in tetrahydrofuran (20 mL). Upon completion by TLC of the reaction, it was poured into a saturated solution of ammonium chloride (200 mL), extracted with ethyl acetate (100 mL), dried with magnesium sulfate, and concentrated. Trituration of the residue with ethyl acetate/dichloromethane gave 5-(4,4-diethyl-2-oxo-1,4-dihydro-2H-3,1-benzoxazin-6-yl)-1-methyl-1H-pyrrole-2-carbonitrile (1.2 g, 55%) as an off-white solid. $^1$H NMR (DMSO-$d_6$): δ 10.26 (s, 1H), 7.37 (d, 1H, J=8.2, 1.6 Hz), 7.31 (d, 1H, J=1.8 Hz), 7.03 (d, 1H, J=4.0 Hz), 6.96 (d, 1H, J=8.2 Hz), 6.32 (d, 1H, J=4.0 Hz), 3.69 (s, 3H), 2.02 (m, 2H, J=7.3 Hz), 1.88 (m, 2H, J=7.3 Hz), 0.78 (t, 6H, J=7.3 Hz). MS (ESI) m/z 310 ([M+H]$^+$); MS (ESI) m/z 308 ([M−H]$^−$). HRMS: calcd for $C_{18}H_{19}N_3O_2$, 309.1477; found (ESI_FT), 310.15488;

5-(4,4-diethyl-2-oxo-1,4-dihydro-2H-3,1-benzoxazin-6-yl)-1-methyl-1H-pyrrole-2-carbonitrile (0.5 g, 1.6 mmol) and Lawesson's Reagent (0.33 g, 0.81 mmol) were heated to 100° C. in toluene (20 mL). Upon completion by TLC, the reaction was poured into saturated sodium carbonate (100 mL) and extracted with ethyl acetate (50 mL), dried over magnesium sulfate, and concentrated. The purification with column gave 5-(4,4-diethyl-2-thioxo-1,4-dihydro-2H-3,1-benzoxazin-6-yl)-1-methyl-1H-pyrrole-2-carbonitrile (0.040 g, 8%) as a tan solid. $^1$H NMR (DMSO-$d_6$): δ 12.15 (s, 1H), 7.44 (d, 1H, J=8.3, 1.8 Hz), 7.37 (d, 1H, J=1.8 Hz), 7.12 (d, 1H, J=8.3 Hz), 7.04 (d, 1H, J=4.03 Hz), 6.35 (d, 1H, J=4.2 Hz), 3.7 (s, 3H), 2.07 (m, 2H, J=7.4 Hz), 1.95 (m, 2H, J=7.4 Hz), 0.79 (t, 6H, J=7.4 Hz). MS (ESI) m/z 326 ([M+H]+); MS (ESI) m/z 324 ([M−H]−). HRMS: calcd for $C_{18}H_{19}N_3OS$, 325.1249; found (ESI_FT), 326.13187.

EXAMPLE 3

5-(4-ethyl-4-methyl-2-thioxo-1,4-dihydro-2H-3,1-benzoxazin-6-yl)-1-methyl-1H-pyrrole-2-carbonitrile A. 6-Bromo-4-ethyl-4-methyl-1,4-dihydro-2H-3,1-benzoxazin-2-one To a stirred solution of 1-(2-amino-5-bromophenyl)-ethanone (10.00 g, 46.70 mmol) in THF (150 mL) was added 3.0M ethyl magnesium bromide (50 mL, 150 mmol) slowly at 0° C. over 20 minutes. The reaction was stirred 1 hr at 0° C., quenched with ammonium chloride solution (sat.) and extracted with ethyl acetate several times. The organic layer was washed with brine and dried over magnesium sulfate. The concentrated crude material was dissolved in THF (150 mL). 1,1'-Carbonyldiimidazole (9.00 g, 56.04 mmol) was added and the reaction was stirred overnight at room temperature. The reaction was partitioned between ammonium chloride solution (sat.) and ethyl acetate. The organic layer was dried over magnesium sulfate and concentrated. Flash silica gel column separation with 30% ethyl acetate/hexane followed by trituration with ether gave 6-bromo-4-ethyl-4-methyl-1,4-dihydro-2H-3,1-benzoxazin-2-one as a white solid (5.84 g, 46%). $^1$H NMR (DMSO-$d_6$): δ 10.28 (s, 1H), 7.43 (m, 2H), 6.783 (d, J=8.3 Hz, 1H), 2.02 (m, 1H), 1.87 (m, 1H), 1.57 (s, 3H), 0.82 (t, J=7.3 Hz, 3H). MS (ESI) m/z 270/272 ([M+H]$^+$); MS (ESI) m/z 268/270 ([M−H]$^−$); HRMS: calcd for $C_{11}H_{12}BrNO_2$, 269.0051; found (ESI_FT), 270.01259. Anal. Calcd for $C_{11}H_{12}BrNO_2$: C, 48.91; H, 4.48; N, 5.19. Found: C, 48.94; H, 4.38; N, 5.00.

B. 5-(4-Ethyl-4-methyl-2-oxo-1,4-dihydro-2H-3,1-benzoxazin-6-yl)-1-methyl-1H-pyrrole-2-carbonitrile Prepared from 6-bromo-4-ethyl-4-methyl-1,4-dihydro-2H-3, 1-benzoxazin-2-one and 1-methyl-1H-pyrrole-2-carbonitrile according to procedure of example 1. $^1$H NMR (DMSO-$d_6$): δ 10.32 (s, 1H), 7.39 (dd, J=8.2, 2.0 Hz, 1H), 7.36 (d, J=2.0 Hz, 1H), 7.03 (d, J=4.2 Hz, 1H), 6.98 (d, J=8.1 Hz, 1H), 6.33 (d, J=4.0 Hz, 1H), 3.70 (s, 3H), 2.06 (m, 1H), 1.90 (m, 1H), 1.61 (s, 3H), 0.85 (t,J=7.3 Hz, 3H). MS (ESI) m/z 296 ([M+H]$^+$); MS (ESI) m/z 294 ([M−H]$^−$). HRMS: calcd for $C_{17}H_{17}N_3O_2$, 295.1321; found (ESI_FT), 296.13872. Anal. Calcd for $C_{17}H_{17}N_3O_2$: C, 69.14; H, 5.80; N, 14.23. Found: C, 68.89; H, 5.60; N, 13.98.

The title compound was prepared from 5-(4-ethyl-4-methyl-2-oxo-1,4-dihydro-2H-3,1-benzoxazin-6-yl)-1-methyl-1H-pyrrole-2-carbonitrile. $^1$H NMR (DMSO-$d_6$): δ 12.23 (s, 1H), 7.47 (dd, J=8.2,1.2Hz, 1H), 7.42 (d, J=1.3 Hz, 1H) 7.14 (d, J=8.3 Hz, 1H), 7.04 (dd, J=4.2, 0.7 Hz, 1H), 6.37 (dd, J=4.2, 0.7 Hz, 1H), 3.71 (s, 3H), 2.08 (m, 1H), 1.95 (m, 1H), 1.67 (s, 3H), 0.87 (t, J=7.3 Hz, 3H). MS (ESI) m/z 312 ([M+H]$^+$); MS (ESI) m/z 310 ([M−H]$^−$); HRMS: calcd for $C_{17}H_{17}N_3OS$, 311.1092; found (ESI_FT), 312.11619. Anal. Calcd for $C_{17}H_{17}N_3OS$: C, 65.57; H, 5.50; N, 13.49. Found: C, 65.29; H, 5.51; N, 13.24.

EXAMPLE 4

1-Methyl-5-(2-thioxo-1,2-dihydrospiro[3,1-benzoxazine-4,1'-cyclohexan]-6-yl)-1H-pyrrole-2-carbonitrile A. 1-Methyl-5-(2-oxo-1,2-dihydrospiro [3,1-benzoxazine-4,1'-cyclohexan]-6-yl)-1H-pyrrole-2-carbonitrile Prepared from 6-bromospiro[4H-3,1-benzoxazine-4,1'-cyclohexan]-2(1H)-one and 1-methyl-1H-pyrrole-2-carbonitrile according to the procedure of example 1. $^1$H NMR (DMSO-$d_6$): δ 10.33 (s, 1H), 7.40 (m, 2H), 7.03 (d, J=4.0 Hz, 1H), 6.98 (d, J=8.2 Hz, 1H), 6.33 (d, J=4.0 Hz, 1H), 3.70 (s, 3H), 2.0 (d, J=5.2 Hz, 2H), 1.97 (td, J=13.5, 4.0 Hz, 2H), 1.76 (m, 4H), 1.67 (m, 2H). MS (ESI) m/z 322 ([M+H]$^+$); MS (ESI) m/z 320 ([M−H]$^−$). HRMS: calcd for $C_{19}H_{19}N_3O_2$, 321.1477; found (ESI_FT), 322.15457; Anal. Calcd for $C_{19}H_{19}N_3O_2$: C, 71.01; H, 5.96; N, 13.07. Found: C, 70.59; H, 5.53; N, 12.38.

The title compound was prepared from 1-methyl-5-(2-oxo-1,2-dihydrospiro [3,1-benzoxazine-4,1'-cyclohexan]-6-yl)-1H-pyrrole-2-carbonitrile according to the procedure of example 1. $^1$H NMR (DMSO-$d_6$): δ 12.29 (s, 1H), 7.47 (m, 2H), 7.14 (d, J=7.3 Hz, 1H), 7.04 (d, J=4.2 Hz, 1H), 6.37 (d, J=4.0 Hz, 1H), 3.71 (s, 3H), 2.03 (d, J=13.2 Hz, 2H), 1.95

(td, J=12.7, 3.9 Hz, 2H), 1.82 (m, 4H), 1.63 (d, J=12.5 Hz, 2H). MS (ESI) m/z 338 ([M+H]$^+$); MS (ESI) m/z 336 ([M–H]$^-$); HRMS: calcd for $C_{19}H_{19}N_3OS$, 337.1249; found (ESI_FT), 338.13141.

EXAMPLE 5

1-Methyl-5-(2-thioxo-1,2-dihydrospiro [3,1-benzoxazine-4,1'-cyclopentan]-6-yl)-1H-pyrrole-2-carbonitrile A. 1-Methyl-5-(2-oxo-1,2-dihydrospiro[3,1-benzoxazine-4,1'-cyclopentan]-6-yl)-1H-pyrrole-2-carbonitrile Prepared from 6-bromospiro[4H-3,1-benzoxazine-4,1'-cyclopentan]-2(1H)-one and 1-methyl-1H-pyrrole-2-carbonitrile according to the procedure of example 1. $^1$H NMR (DMSO-d$_6$): δ 10.35 (s, 1H), 7.40 (m, 2H), 7.02 (d, J=4.2Hz, 1H), 6.99 (d, J=8.4 Hz, 1H), 6.34 (d, J=4.0 Hz, 1H), 3.70 (s, 3H), 2.15 (m, 4H), 1.89 (m, 4H). MS (ESI) m/z 308 ([M+H]$^+$); MS (ESI) m/z 306 ([M–H]$^-$); HRMS: calcd for $C_{18}H_{17}N_3O_2$, 307.1321; found (ESI_FT), 308.13868; Anal. Calcd for $C_{18}H_{17}N_3O_2$: C, 70.34; H, 5.58; N, 13.67. Found: C, 70.27; H, 5.57; N, 13.74.

The title compound was prepared from 1-methyl-5-(2-oxo-1,2-dihydrospiro[3,1-benzoxazine-4,1'-cyclopentan]-6-yl)-1H-pyrrole-2-carbonitrile according to the procedure of example 1. $^1$H NMR (DMSO-d$_6$): δ 12.29 (s, 1H), 7.48 (m, 2H), 7.14 (d, J=8.7 Hz, 1H), 7.04 (d, J=4.0 Hz, 1H), 6.38 (d, J=4.2 Hz, 1H), 3.71 (s, 3H), 2.19 (m, 4H), 1.93 (m, 4H). MS (ESI) m/z 324 ([M+H]$^+$); MS (ESI) m/z 322 ([M–H]$^-$); HRMS: calcd for $C_{18}H_{17}N_3OS$, 323.1092; found (ESI_FT), 324.11637; Anal. Calcd for $C_{18}H_{17}N_3OS$: C, 66.85; H, 5.30; N, 12.99. Found: C, 65.84; H, 5.22; N, 12.30.

EXAMPLE 6

1-Methyl-5-[2-thioxo-4,4-bis(trifluoromethyl)-1,4-dihydro-2H-3,1-benzoxazin-6-yl]-1H-pyrrole-2-carbonitrile A. 2-(2-Aminophenyl)-1,1,1,3,3,3-hexafluoropropan-2-ol To a stirred solution of phenylcarbamic acid tert-butyl ester (2.00 g, 10.35 mmol) in ether (20 mL) was added 1.7M tert-butyl lithium (14 mL, 22.80 mmol) at –10° C. The reaction was stirred for 3 hrs at –10° C., cooled to –78° C. and gaseous hexafluoroacetone was bubbled into the solution for 5 minutes. The reaction was allowed to warm to room temperature, quenched with ammonium chloride solution (sat.) and extracted with ethyl acetate. The organic layer was dried over magnesium sulfate and concentrated. The crude concentrate was stirred in excess trifluoroacetic acid for 20 minutes. The solution was concentrated, neutralized with sodium bicarbonate solution (sat.) and extracted several times with ethyl acetate. The organic layer was dried over magnesium sulfate and concentrated to give 4.20 g of 2-(2-aminophenyl)-1,1,1,3,3,3-hexafluoropropan-2-ol as white solid (52%). $^1$H NMR (DMSO-d$_6$): δ 9.29 (s, 1H), 7.16 (m, 2H), 6.77 (dd, J=8.2, 1.2 Hz, 1H), 6.62 (m, 1H), 5.63 (br s, 2H). MS (ESI) m/z 260 ([M+H]$^+$); MS (ESI) m/z 258 ([M–H]$^-$); HRMS: calcd for $C_9H_7F_6NO$, 259.0432; found (ESI_FT), 260.04993.

B. 4,4-bis(Trifluoromethyl)-1,4-dihydro-2H-3,1-benzoxazin-2-one

To a stirred solution of 2-(2-aminophenyl)-1,1,1,3,3,3-hexafluoropropan-2-ol (4.20 g, 16.20 mmol) in THF (160 mL) was added triphosgene (4.80 g, 16.20 mmol). The reaction was stirred overnight, quenched with ammonium chloride solution (sat.) and extracted several times with ethyl acetate. The organic layer was dried over magnesium sulfate and triturated with ether/hexane to give 2.78 g of 4,4-bis(trifluoromethyl)-1,4-dihydro-2H-3,1-benzoxazin-2-one as a tan solid (60%). $^1$H NMR (DMSO-d$_6$): δ 11.37 (s, 1H), 7.62 (m, 2H), 7.29 (t, J=7.5 Hz, 1H), 7.11 (dd, J=8.0, 0.8 Hz, 1H). MS (ESI) m/z 284 ([M–H]$^-$); HRMS: calcd for $C_{10}H_5F_6NO_2$, 285.0224; found (ESI_FT), 286.0299; Anal. Calcd for $C_{10}H_5F_6NO_2$: C, 42.12; H, 1.77; N, 4.91. Found: C, 42.63; H, 1.79; N, 4.72.

C. 6-Bromo-4,4-bis(trifluoromethyl)-1,4-dihydro-2H-3,1-benzoxazin-2-one

To a stirred solution of 4,4-bis(trifluoromethyl)-1,4-dihydro-2H-3,1-benzoxazin-2-one (0.50 g, 1.75 mmol) in glacial acetic acid (6 mL) buffered with potassium acetate (0.52 g, 5.25 mmol) was added bromine (0.28 g, 1.75 mmol). The reaction was stirred 30 minutes and poured into brine (30 mL), and extracted with ethyl acetate several times. The organic layer was dried over magnesium sulfate and concentrated. Flash column separation using 10% ethyl acetate/hexane gave 0.36 g of 6-bromo-4,4-bis(trifluoromethyl)-1,4-dihydro-2H-3,1-benzoxazin-2-one as a white solid (57%). $^1$H NMR (DMSO-d$_6$): δ 11.57 (s, 1H), 7.85 (dd, J=8.7, 2.2 Hz, 1H), 7.60 (s, 1H), 7.08 (d, J=8.7 Hz, 1H). MS (ESI) m/z 362/364 ([M+H]$^+$); HRMS: calcd for $C_{10}H_4BrF_6NO_2$, 362.9330; found (ESI_FT), 363.93994.

D. 1-Methyl-5-[2-oxo-4,4-bis(trifluoromethyl)-1,4-dihydro-2H-3,1-benzoxazin-6-yl]-1H-pyrrole-2-carbonitrile Prepared from 6-bromo-4,4-bis(trifluoromethyl)-1,4-dihydro-2H-3,1-benzoxazin-2-one and 1-methyl-1H-pyrrole-2-carbonitrile according to the procedure of example 1. $^1$H NMR (DMSO-d$_6$): δ 11.59 (s, 1H), 7.78 (dd, J=8.5, 2.0 Hz, 1H), 7.57 (s, 1H), 7.22 (d, J=8.4 Hz, 1H), 7.06 (d, J=4.0 Hz, 1H), 6.39 (d, J=4.2 Hz, 1H), 3.69 (s, 3H). MS (ESI) m/z 388 ([M–H]$^-$); HRMS: calcd for $C_{16}H_9F_6N_3O_2$, 389.0599; found (ESI_FT), 390.0659.

The title compound was prepared from 1-methyl-5-[2-oxo-4,4-bis(trifluoromethyl)-1,4-dihydro-2H-3,1-benzoxazin-6-yl]-1H-pyrrole-2-carbonitrile according to the procedure of example 1. $^1$H NMR (DMSO-d$_6$): δ 13.43 (s, 1H), 7.85 (dd, J=8.5, 1.8 Hz, 1H), 7.62 (s, 1H), 7.37 (d, J=8.6 Hz, 1H), 7.07 (d, J=4.0 Hz, 1H), 6.44 (d, J=4.2 Hz, 1H), 3.70 (s, 3H). MS (ESI) m/z 406 ([M+H]$^+$); MS (ESI) m/z 404 ([M–H]$^-$); HRMS: calcd for $C_{16}H_9F_6N_3OS$, 405.0370; found (ESI_FT), 406.04395.

EXAMPLE 7

Pharmacology

The compounds useful in this invention are tested in the relevant assay as described below and their potency are in the range of 0.01 nM to 5 μM in the in vitro assays and 0.001 to 300 mg/kg in the in vivo assays. Selected compounds within formula II, including those described in Examples 1-6 above, have been found to have potency in the range of 0.1 to 1 nM in a functional in vitro assays as described below.

A. In-vitro Biology

The in-vitro biology is determined by (1) competitive Radioligand Binding: using the A-form of the human progesterone receptor with progesterone as the radioligand; (2) co-transfection assay, which provides functional activity expressed as agonist EC50 and Antagonist IC50 values; (3) a T47D cell proliferation, which is a further functional assay which also provides agonist and antagonist data; and (4)

T47D cell alkaline phosphatase assay, which is a further functional assay which also provides agonist and antagonist data.

1. hPR Binding assay—This assay is carried out in accordance with: Pathirana, C.; Stein, R. B.; Berger, T. S.; Fenical, W.; Ianiro, T.; Mais, D. E.; Torres, A.; Glodman, M. E., Nonsteroidal human progesterone receptor modulators from the marine alga cymoplia barbata, J. Steroid Biochem. Mol. Biol., 1992, 41, 733-738.

2. PRE-luciferase Assay in CV-1 Cells

The object of this assay is to determine a compound's progestational or antiprogestational potency based on its effect on PRE-luciferase reporter activity in CV-1 cells co-transfected with human PR and PRE-luciferase plasmids. The materials methods used in the assay are as follows.

a. Medium: The growth medium was as follows: DMEM (BioWhittaker) containing 10% (v/v) fetal bovine serum (heat inactivated), 0.1 mM MEM non-essential amino acids, 100 U/ml penicillin, 100 mg/ml streptomycin, and 2 mM GlutaMax (GIBCO, BRL). The experimental medium was as follows: DMEM (BioWhittaker), phenol red-free, containing 10% (v/v) charcoal-stripped fetal bovine serum (heat-inactivated), 0.1 mM MEM non-essential amino acids, 100 U/ml penicillin, 100 mg/ml streptomycin, and 2 mM GlutaMax (GIBCO, BRL).

b. Cell Culture, Transfection, Treatment, and Luciferase assay

Stock CV-1 cells are maintained in growth medium. Co-transfection is done using $1.2 \times 10^7$ cells, 5 mg pLEM plasmid with hPR-B inserted at Sph1 and BamH1 sites, 10 mg pGL3 plasmid with two PREs upstream of the luciferase sequence, and 50 mg sonicated calf thymus DNA as carrier DNA in 250 ml. Electroporation is carried out at 260 V and 1,000 mF in a Biorad Gene Pulser II. After electroporation, cells are resuspended in growth medium and plated in 96-well plate at 40,000 cells/well in 200 μl. Following overnight incubation, the medium is changed to experimental medium. Cells are then treated with reference or test compounds in experimental medium. Compounds are tested for antiprogestational activity in the presence of 3 nM progesterone. Twenty-four hr. after treatment, the medium is discarded, cells are washed three times with D-PBS (GIBCO, BRL). Fifty μl of cell lysis buffer (Promega, Madison, Wis.) is added to each well and the plates are shaken for 15 min in a Titer Plate Shaker (Lab Line Instrument, Inc.). Luciferase activity is measured using luciferase reagents from Promega.

c. Analysis of Results.

Each treatment consists of at least 4 replicates. Log transformed data are used for analysis of variance and nonlinear dose response curve fitting for both agonist and antagonist modes. Huber weighting is used to downweight the effects of outliers. $EC_{50}$ or $IC_{50}$ values are calculated from the retransformed values. JMP software (SAS Institute, Inc.) is used for both one-way analysis of variance and non-linear response analyses.

d. Reference Compounds.

Progesterone and trimegestone are reference progestins and RU486 is the reference antiprogestin. All reference compounds are run in full dose-response curves and the $EC_{50}$ or $IC_{50}$ values are calculated.

TABLE 1

Estimated $EC_{50}$, standard error (SE), and 95% confidence intervals (CI) for reference progestins from three individual studies

| Compound | Exp. | $EC_{50}$ (nM) | SE | 95% CI lower | 95% CI upper |
|---|---|---|---|---|---|
| Progesterone | 1 | 0.616 | 0.026 | 0.509 | 0.746 |
|  | 2 | 0.402 | 0.019 | 0.323 | 0.501 |
|  | 3 | 0.486 | 0.028 | 0.371 | 0.637 |
| Trimegestone | 1 | 0.0075 | 0.0002 | 0.0066 | 0.0085 |
|  | 2 | 0.0081 | 0.0003 | 0.0070 | 0.0094 |
|  | 3 | 0.0067 | 0.0003 | 0.0055 | 0.0082 |

TABLE 2

Estimated $IC_{50}$, standard error (SE), and 95% confident interval (CI) for the antiprogestin, RU486 from three individual studies

| Compound | Exp. | IC 50 (nM) | SE | 95% CI lower | 95% CI upper |
|---|---|---|---|---|---|
| RU486 | 1 | 0.028 | 0.002 | 0.019 | 0.042 |
|  | 2 | 0.037 | 0.002 | 0.029 | 0.048 |
|  | 3 | 0.019 | 0.001 | 0.013 | 0.027 |

Progestational activity: Compounds that increase PRE-luciferase activity significantly ($p<0.05$) compared to vehicle control are considered active.

Antiprogestational activity: Compounds that decrease 3 nM progesterone induced PRE-luciferase activity significantly ($p<0.05$)

$EC_{50}$: Concentration of a compound that gives half-maximal increase PRE-luciferase activity (default-nM) with SE.

$IC_{50}$: Concentration of a compound that gives half-maximal decrease in 3 nM progesterone induced PRE-luciferase activity (default-nM) with SE.

3. T47D cell Proliferation Assay

The objective of this assay is the determination of progestational and antiprogestational potency by using a cell proliferation assay in T47D cells. A compound's effect on DNA synthesis in T47D cells is measured. The materials and methods used in this assay are as follows.

a. Growth Medium: DMEM:F12 (1:1) (GIBCO, BRL) supplemented with 10% (v/v) fetal bovine serum (not heat-inactivated), 100 U/ml penicillin, 100 mg/ml streptomycin, and 2 mM GlutaMax (GIBCO, BRL).

b. Treatment Medium: Minimum Essential Medium (MEM) (#51200-038GIBCO, BRL) phenol red-free supplemented with 0.5% charcoal stripped fetal bovine serum, 100 U/ml penicillin, 200 mg/ml streptomycin, and 2 mM GlutaMax (GIBCO, BRL).

c. Cell Culture

Stock T47 D cells are maintained in growth medium. For BrdU incorporation assay, cells are plated in 96-well plates (Falcon, Becton Dickinson Labware) at 10,000 cells/well in growth medium. After overnight incubation, the medium is changed to treatment medium and cells are cultured for an additional 24 hr before treatment. Stock compounds are dissolved in appropriate vehicle (100% ethanol or 50% ethanol/50% DMSO), subsequently diluted in treatment medium and added to the cells. Progestin and antiprogestin reference compounds are run in full dose-response curves. The final concentration of vehicle is 0.1%. In control wells, cells receive vehicle only. Antiprogestins are tested in the presence of 0.03 nM trimegestone, the reference progestin agonist. Twenty-four hours after treatment, the medium is discarded and cells are labeled with 10 mM BrdU (Amersham Life Science, Arlington Heights, Ill.) in treatment medium for 4 hr.

d. Cell Proliferation Assay

At the end of BrdU labeling, the medium is removed and BrdU incorporation is measured using a cell proliferation ELISA kit (#RPN 250, Amersham Life Science) according to manufacturer's instructions. Briefly, cells are fixed in an ethanol containing fixative for 30 min, followed by incubation in a blocking buffer for 30 min to reduce background. Peroxidase-labeled anti-BrdU antibody is added to the wells and incubated for 60 min. The cells are rinsed three times with PBS and incubated with 3,3'5,5'-tetramethylbenzidine (TMB) substrate for 10-20 min depending upon the potency of tested compounds. Then 25 µl of 1 M sulfuric acid is added to each well to stop color reaction and optical density is read in a plate reader at 450 nm within 5 min.

e. Analysis of Results:

Square root-transformed data are used for analysis of variance and nonlinear dose response curve fitting for both agonist and antagonist modes. Huber weighting is used to downweight the effects of outliers. $EC_{50}$ or $IC_{50}$ values are calculated from the retransformed values. JMP software (SAS Institute, Inc.) is used for both one-way analysis of variance and non-linear dose response analyses in both single dose and dose response studies.

f. Reference Compounds:

Trimegestone and medroxyprogesterone acetate (MPA) are reference progestins and RU486 is the reference antiprogestin. All reference compounds are run in full dose-response curves and the $EC_{50}$ or $IC_{50}$ values are calculated.

TABLE 3

Estimated $EC_{50}$, standard error (SE), and 95% confidence intervals (CI) for individual studies

| Compound | Exp | $EC_{50}$ (nM) | SE | 95% CI lower | 95% CI upper |
|---|---|---|---|---|---|
| Trimegestone | 1 | 0.017 | 0.003 | 0.007 | 0.040 |
|  | 2 | 0.014 | 0.001 | 0.011 | 0.017 |
|  | 3 | 0.019 | 0.001 | 0.016 | 0.024 |
| MPA | 1 | 0.019 | 0.001 | 0.013 | 0.027 |
|  | 2 | 0.017 | 0.001 | 0.011 | 0.024 |

TABLE 4

Estimated $IC_{50}$, standard error, and 95% confident interval for the antiprogestin, RU486

| Compound | Exp | $IC_{50}$ (nM) | SE | 95% CI lower | 95% CI upper |
|---|---|---|---|---|---|
| RU486 | 1 | 0.011 | 0.001 | 0.008 | 0.014 |
|  | 2 | 0.016 | 0.001 | 0.014 | 0.020 |
|  | 3 | 0.018 | 0.001 | 0.014 | 0.022 |

$EC_{50}$: Concentration of a compound that gives half-maximal increase in BrdU incorporation with SE; $IC_{50}$: Concentration of a compound that gives half-maximal decrease in 0.1 trimegestone induced BrdU incorporation with SE 4. T47D Cell Alkaline Phosphatase Assay The purpose of this assay is to identify progestins or antiprogestins by determining a compound's effect on alkaline phosphatase activity in T47D cells. The materials and methods used in this assay are as follows.

a. Culture Medium: DMEM:F12 (1:1) (GIBCO, BRL) supplemented with 5% (v/v) charcoal stripped fetal bovine serum (not heat-inactivated), 100 U/ml penicillin, 100 µg/ml streptomycin, and 2 mM GlutaMax (GIBCO, BRL).

b. Alkaline Phosphatase Assay Buffer:

I. 0.1 M Tris-HCl, pH 9.8, containing 0.2% Triton X-100

II. 0.1 M Tris-HCl, pH 9.8 containing 4 mM p-nitrophenyl phosphate (Sigma).

c. Cell Culture and Treatment:

Frozen T47D cells were thawed in a 37° C. water bath and diluted to 280,000 cells/ml in culture medium. To each well in a 96-well plate (Falcon, Becton Dickinson Labware), 180 µl of diluted cell suspension was added. Twenty µl of reference or test compounds diluted in the culture medium was then added to each well. When testing for progestin antagonist activity, reference antiprogestins or test compounds were added in the presence of 1 nM progesterone. The cells were incubated at 37° C. in a 5% $CO_2$/humidified atmosphere for 24 hr.

d. Alkaline Phosphatase Enzyme Assay:

At the end of treatment, the medium was removed from the plate and fifty VII of assay buffer I was added to each well. The plates were shaken in a titer plate shaker for 15 min. Then 150 µl of assay buffer II was added to each well. Optical density measurements were taken at 5 min intervals for 30 min at a test wavelength of 405 nM.

e. Analysis of Results: Analysis of Dose-response Data

For reference and test compounds, a dose response curve is generated for dose (X-axis) vs. the rate of enzyme reaction (slope) (Y-axis). Square root-transformed data are used for analysis of variance and nonlinear dose response curve fitting for both agonist and antagonist modes. Huber weighting is used to downweight the effects of outliers. $EC_{50}$ or $IC_{50}$ values are calculated from the retransformed values. JMP software (SAS Institute, Inc.) is used for both one-way analysis of variance and non-linear dose response analyses in both single dose and dose response studies.

f. Reference Compounds:

Progesterone and trimegestone are reference progestins and RU486 is the reference antiprogestin. All reference compounds are run in full dose response curves and the $EC_{50}$ or $IC_{50}$ values are calculated.

TABLE 5

Estimated $EC_{50}$, standard error (SE), and 95% confidence intervals (CI) for reference progestins from three independent experiments

| Compound | Exp. | $EC_{50}$ (nM) | SE | 95% CI lower | 95% CI upper |
|---|---|---|---|---|---|
| Progesterone | 1 | 0.839 | 0.030 | 0.706 | 0.996 |
|  | 2 | 0.639 | 0.006 | 0.611 | 0.669 |
|  | 3 | 1.286 | 0.029 | 1.158 | 1.429 |
| Trimegestone | 1 | 0.084 | 0.002 | 0.076 | 0.091 |
|  | 2 | 0.076 | 0.001 | 0.072 | 0.080 |
|  | 3 | 0.160 | 0.004 | 0.141 | 0.181 |

TABLE 6

Estimated $IC_{50}$, standard error, and 95% confident interval for the reference antiprogestin RU486 from three independent experiments

| Compound | Exp | IC 50 (nM) | SE | 95% CI lower | upper |
|---|---|---|---|---|---|
| RU486 | 1 | 0.103 | 0.002 | 0.092 | 0.115 |
|  | 2 | 0.120 | 0.001 | 0.115 | 0.126 |
|  | 3 | 0.094 | 0.007 | 0.066 | 0.134 |

For the test compounds listed below, the following data were obtained in the T47D alkaline phosphatase assay described herein.

| | |
|---|---|
| 5-(4-ethyl-4-methyl-2-thioxo-1,4-dihydro-2H-3,1-benzoxazin-6-yl)-1-methyl-1H-pyrrole-2-carbonitrile: | EC50 = 0.1 nM |
| 5-(4,4-diethyl-2-thioxo-1,4-dihydro-2H-3,1-benzoxazin-6-yl)-1-methyl-1H-pyrrole-2-carbonitrile: | EC50 = 0.1 nM |
| 1-methyl-5-(2-thioxo-1,2-dihydrospiro[3,1-benzoxazine-4,1'-cyclobutan]-6-yl)-1H-pyrrole-2-carbonitrile: | EC50 = 0.5 nM |
| 1-methyl-5-(2-thioxo-1,2-dihydrospiro[3,1-benzoxazine-4,1'-cyclohexan]-6-yl)-1H-pyrrole-2-carbonitrile: | EC50 = 0.3 nM |
| 1-methyl-5-(2-thioxo-1,2-dihydrospiro[3,1-benzoxazine-4,1'-cyclopentan]-6-yl)-1H-pyrrole-2-carbonitrile: | EC50 = 0.5 nM |
| 1-methyl-5-[2-thioxo-4,4-bis(trifluoromethyl)-1,4-dihydro-2H-3,1-benzoxazine-6-yl]-1H-pyrrole-2-carbonitrile: | EC50 < 10 nM |

B. In-vivo Biology

The primary in-vivo assay is the rat decidualization model which may be used to determine progestational effects of both agonists and antagonists. The secondary in-vivo assay is the rat ovulation inhibition model which is under development and hence the protocol is un-available.

1. Rat decidualization assay: The objective of this procedure is used to evaluate the effect of progestins and antiprogestins on rat uterine decidualization and compare the relative potencies of various test compounds. The materials and methods used in this assay are as follows.

a. Methods: Test compounds are dissolved in 100% ethanol and mixed with corn oil (vehicle). Stock solutions of the test compounds in oil (Mazola™) are then prepared by heating (~80° C.) the mixture to evaporate ethanol. Test compounds are subsequently diluted with 100% corn oil or 10% ethanol in corn oil prior to the treatment of animals. No difference in decidual response was found when these two vehicles were compared.

b. Animals (RACUC Protocol #5002)

Ovariectomized mature female Sprague-Dawley rats (~60-day old and 230 g) are obtained from Taconic (Taconic Farms, N.Y.) following surgery. Ovariectomy is performed at least 10 days prior to treatment to reduce circulating sex steroids. Animals are housed under 12 hr light/dark cycle and given standard rat chow and water ad libitum.

c. Treatment

Rats are weighed and randomly assigned to groups of 4 or 5 before treatment. Test compounds in 0.2 ml vehicle are administered by subcutaneous injection in the nape of the neck or by gavage using 0.5 ml. The animals are treated once daily for seven days. For testing antiprogestins, animals are given the test compounds and a $EC_{50}$ dose of progesterone (5.6 mg/kg) during the first three days of treatment. Following decidual stimulation, animals continue to receive progesterone until necropsy four days later.

d. Dosing

Doses are prepared based upon mg/kg mean group body weight. In all studies, a control group receiving vehicle is included. Determination of dose-response curves is carried out using doses with half log increases (e.g. 0. 1, 0.3, 1.0, 3.0 mg/kg).

e. Decidual Induction

Approximately 24 hr after the third injection, decidualization is induced in one of the uterine horns by scratching the antimesometrial luminal epithelium with a blunt 21 G needle. The contralateral horn is not scratched and serves as an unstimulated control. Approximately 24 hr following the final treatment, rats are sacrificed by $CO_2$ asphyxiation and body weight measured. Uteri are removed and trimmed of fat. Decidualized (D-horn) and control (C-horn) uterine horns are weighed separately.

f. Analysis of Results:

The increase in weight of the decidualized uterine horn is calculated by D-horn/C-horn and logarithmic transformation is used to maximize normality and homogeneity of variance. The Huber M-estimator is used to down weight the outlying transformed observations for both dose-response curve fitting and one-way analysis of variance. JMP software (SAS Institute, Inc.) is used for both one-way ANOVA and non-linear dose-response analyses.

g. Reference Compounds.

All progestin reference compounds were run in full dose response curves and the $EC_{50}$ for uterine wet weight were calculated.

TABLE 7

Estimated $EC_{50}$, standard error (SE), and 95% confidence intervals for individual studies

| Compound | Exp | EC$_{50}$ (mg/kg, s.c.) | SE | 95% CI lower | upper |
|---|---|---|---|---|---|
| Progesterone | 1 | 5.50 | 0.77 | 4.21 | 7.20 |
|  | 2 | 6.21 | 1.12 | 4.41 | 8.76 |
| 3-Ketodesogestrel | 1 | 0.11 | 0.02 | 0.07 | 0.16 |
|  | 2 | 0.10 | 0.05 | 0.11 | 0.25 |
|  | 3 | 0.06 | 0.03 | 0.03 | 0.14 |
| Levonorgestrel | 1 | 0.08 | 0.03 | 0.04 | 0.16 |
|  | 2 | 0.12 | 0.02 | 0.09 | 0.17 |
|  | 3 | 0.09 | 0.02 | 0.06 | 0.13 |
|  | 4 | 0.09 | 0.02 | 0.06 | 0.14 |
| MPA | 1 | 0.42 | 0.03 | 0.29 | 0.60 |
|  | 2 | 0.39 | 0.05 | 0.22 | 0.67 |
|  | 3 | 0.39 | 0.04 | 0.25 | 0.61 |

TABLE 8

Estimated average $EC_{50}$, standard error, and 95% confidence intervals for dose-response curves of 3 reference compounds

| Compound | EC50 (mg/kg, s.c.) | SE | 95% CI lower | upper |
|---|---|---|---|---|
| Progesterone | 5.62 | 0.62 | 4.55 | 7.00 |
| 3-Ketodesogestrel | 0.10 | 0.02 | 0.07 | 0.14 |
| Levonorgestrel | 0.10 | 0.01 | 0.08 | 0.12 |

TABLE 9

Estimated $IC_{50}$, standard error, and 95% confident interval for the antiprogestin, RU 486

| Compound | Exp. | $IC_{50}$ (mg/kg, p.o.) | SE | 95% CI lower | 95% CI upper |
|---|---|---|---|---|---|
| RU 486 | 1 | 0.21 | 0.07 | 0.05 | 0.96 |
|  | 2 | 0.14 | 0.02 | 0.08 | 0.27 |

Concentration: Compound concentration in assay(default-mg/kg body weight)

Route of administration: Route the compound is administered to the animals

Body weight: Mean total animal body weight (default-kg)

D-horn: Wet weight of decidualized uterine horn (default-mg)

C-horn: Wet weight of control uterine horn (default-mg)

Decidual response: $[(D-C)/C] \times 100\%$

Progestational activity: Compounds that induce decidualization significantly (p<0.05) compared to vehicle control are considered active Antiprogestational activity: Compounds that decrease $EC_{50}$ progesterone induced decidualization significantly (p<0.05)

$EC_{50}$ for uterine weight: Concentration of compound that gives half-maximal increase in decidual response (default-mg/kg)

$IC_{50}$ for uterine weight: Concentration of compound that gives half-maximal decrease in $EC_{50}$ progesterone induced decidual response (default-mg/kg)

EXAMPLE 8

Treatment of Acne

A twenty-five year old human patient having acne vulgaris is treated according to the present invention. Specifically, 5-(4,4-dimethyl-2-thioxo-1,4-dihydro-2H-3,1-benzoxazin-6-yl)-1-methyl-1H-pyrrole-2-carbonitrile is orally delivered to the patient daily. Delivery is in the form of a tablet formulated to contain about 20 mg of 5-(4,4-dimethyl-2-thioxo-1,4-dihydro-2H-3,1-benzoxazin-6-yl)-1-methyl-1H-pyrrole-2-carbonitrile.

Forty-five to sixty days after the treatment, a decrease in the presence of lesions caused by acne vulgaris is noticed. After about 24 weeks, improvement in the acne vulgaris is observed.

EXAMPLE 9

Treatment of Hirsutism

Male intact golden Syrian hamsters, which display oval shaped flank organs, one on each side, are utilized to demonstrate hair growth. The flank organs are depilated and/or shaved to remove the initial presence of hair. To one organ is applied a cream containing 5 mg of 5-(4,4-dimethyl-2-thioxo-1,4-dihydro-2H-3,1-benzoxazin-6-yl)-1-methyl-1H-pyrrole-2-carbonitrile. After about thirteen applications, one application per day for five days a week, the flank organs are shaved and the amount of recovered hair from each organ is determined.

From these data, it is determined that the compositions of the invention provide a reduction in hair growth of at least about 15%.

EXAMPLE 10

Conditioning the Skin

A thirty year old human patient having a severe form of eczema is treated according to the present invention. Specifically, about 50 mg of 5-(4,4-dimethyl-2-thioxo-1,4-dihydro-2H-3,1-benzoxazin-6-yl)-1-methyl-1H-pyrrole-2-carbonitrile is delivered to the patient daily.

Thirty days after the treatment, a decrease in the dryness affected to the skin is noticed. After about 12 weeks, improvement in the eczema is observed.

From these data, it is determined that the compositions of the invention are effective in conditioning the skin.

EXAMPLE 11

Anti-androgenic Effect

The androgen receptor (AR) agonistic and antagonistic activity of the compositions of the invention in the L929 cells which express the AR but not the PR was evaluated as described in Zhang et al., Steroids, 65(10-11): 637-643 (October-November 2000).

Cells were plated in 96-well plates at 25,000 cells/well in DMEM (BioWhittaker) with 10% (v/v) fetal bovine serum (FBS). The next day, cells were infected with the adenovirus PRE-tk-luciferase reporter construct ($2 \times 10^9$ pfu/ml particles) and kept in DMEM containing 10% charcoal stripped FBS for an additional 24 hours. Cells were then separately treated with a range of concentrations of the dihydrotestosterone (DHT) reference, the 2-hydroxyflutamide (2-OH-fluta) reference, or 5-(4,4-dimethyl-2-thioxo-1,4-dihydro-2H-3,1-benzoxazin-6-yl)-1-methyl-1H-pyrrole-2-carbonitrile diluted in the same medium. To test the anti-androgenic activity, cells were co-treated with 3 nM DHT. Luciferase activity was measured 24 hours following the treatment. The following data were obtained:

TABLE 10

| Compound | IC50 (nM) |
|---|---|
| 5-(4,4-dimethyl-2-thioxo-1,4-dihydro-2H-3,1-benzoxazin-6-yl)-1-methyl-1H-pyrrole-2-carbonitrile | 109 |
| 2-OH-fluta | 49.9 |

From these data, it was noted that 5-(4,4-dimethyl-2-thioxo-1,4-dihydro-2H-3,1-benzoxazin-6-yl)-1-methyl-1H-pyrrole-2-carbonitrile showed significant antagonistic activity over a nine point dose response and only marginal agonistic activity at the maximum concentration tested (i.e., 10 nM).

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

What is claimed:

1. A method of treating acne or hirsutism comprising the step of delivering to a mammal in need thereof a composition comprising an effective amount of a compound of formula I and a physiographically compatible carrier, wherein said compound of formula I is of the structure:

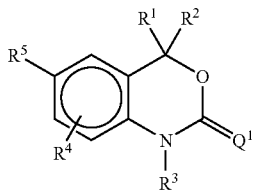

wherein:
- $R^1$ and $R^2$ are independent substituents selected from the group consisting of H, $C_1$ to $C_6$ alkyl, and substituted $C_1$ to $C_6$ alkyl; or
- $R^1$ and $R^2$ are fused to form a carbon-based 3 to 8 membered saturated spirocyclic ring;
- $R^3$ is H;
- $R^4$ is H;
- $R^5$ is a five membered carbon-based heterocyclic ring having in its backbone 1, 2, or 3 $NR^6$ heteroatoms and having one or two independent substituents selected from the group consisting of H, halogen, and CN;
- $R^6$ is selected from the group consisting of H, $C_1$ to $C_3$ alkyl, and $C_1$ to $C_4$ $CO_2$alkyl;
- $Q^1$ is S;

or a pharmaceutically acceptable salt thereof to treat said acne or hirsutism.

2. The method according to claim 1, further comprising delivering an estrogen in combination with the compound of formula I.

3. The method according to claim 2, wherein the estrogen is delivered prior to or subsequent to the compound of formula I.

4. The method according to claim 1, wherein said compound is selected from the group consisting of 5-(4,4-Dimethyl-2-thioxo-1,4-dihydro-2H-3,1-benzoxazin-6-yl)-1H-pyrrole-2-carbonitrile, 5-(4,4-dimethyl-2-thioxo-1,4-dihydro-2H-3,1-benzoxazin-6-yl)-1-ethyl-1H-pyrrole-2-carbonitrile, or a pharmaceutically acceptable salt, thereof.

5. The method according to claim 1, wherein said compound is 5-(4,4-dimethyl-2-thioxo-1,4-dihydro-2H-3,1-benzoxazin-6-yl)-1-methyl-1H-pyrrole-2-carbonitrile, or a pharmaceutically acceptable salt, thereof.

6. The method according to claim 1, wherein $R^1$ and $R^2$ are fused to form a carbon-based 3 to 6 membered saturated spirocyclic ring.

7. The method according to claim 1, wherein said compound is 5-(4-ethyl-4-methyl-2-thioxo-1,4-dihydro-2H-3,1-benzoxazin-6-yl)-1-methyl-1H-pyrrole-2-carbonitrile, 5-(4,4-diethyl-2-thioxo-1,4-dihydro-2H-3,1-benzoxazin-6-yl)-1-methyl-1H-pyrrole-2-carbonitrile, 1-methyl-5-(2-thioxo-1,2-dihydrospiro[3,1-benzoxazine-4,1'-cyclobutan]-6-yl)-1H-pyrrole-2-carbonitrile, 1-methyl-5-(2-thioxo-1,2-dihydrospiro[3,1-benzoxazine-4,1'-cyclohexan]-6-yl)-1H-pyrrole-2-carbonitrile, 1-methyl-5-(2-thioxo-1,2-dihydrospiro[3,1-benzoxazine-4,1'-cyclopentan]-6-yl)-1H-pyrrole-2-carbonitrile, 1-methyl-5-[2-thioxo-4,4-bis(trifluoromethyl)-1,4-dihydro-2H-3,1-benzoxazin-6-yl]-1H-pyrrole-2-carbonitrile or pharmaceutically acceptable salts thereof.

8. A method for treating acne or hirsutism in a mammal comprising administering to said manual in need thereof a composition comprising an effective amount of a compound of formula II represented by the structure:

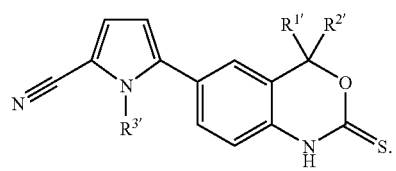

wherein: $R^{1'}$ is selected from the group consisting of methyl, ethyl, and trifluoromethyl; $R^{2'}$ is selected from the group consisting of methyl, ethyl, and trifluoromethyl; or $R^{1'}$ or $R^{2'}$ are fused to form a spirocyclic ring containing 3 to 7 carbon atoms; and $R^{3'}$ is $C_1$ to $C_4$ alkyl; or pharmaceutically acceptable salts thereof to treat said acne or hirsutism.

9. The method accordingly to claim 8, wherein said compound is 5-(4-ethyl-4-methyl-2-thioxo-1,4-dihydro-2H-3,1-benzoxazin-6-yl)-1-methyl-1H-pyrrole-2-carbonitrile, 5-(4,4-diethyl-2-thioxo-1,4-dihydro-2H-3,1-benzoxazin-6-yl)-1-methyl-1H-pyrrole-2-carbonitrile, 1-methyl-5-(2-thioxo-1,2-dihydrospiro[3,1-benzoxazine-4,1'-cyclobutan]-6-yl)-1H-pyrrole-2-carbonitrile, 1-methyl-5-(2-thioxo-1,2-dihydrospiro[3,1-benzoxazine-4,1'-cyclohexan]-6-yl)-1H-pyrrole-2-carbonitrile, 1-methyl-5-(2-thioxo-1,2-dihydrospiro[3,1-benzoxazine-4,1'-cyclopentan]-6-yl)-1H-pyrrole-2-carbonitrile, 1-methyl-5-[2-thioxo-4,4-bis(trifluoromethyl)-1,4-dihydro-2H-3,1-benzoxazine-6-yl)-1H-pyrrole-2-carbonitrile, or pharmaceutically acceptable salts thereof.

10. The method accordingly to claim 8, wherein said compound is 5-(4,4 dimethyl-2-thioxo-1,4-dihydro-2H-3,1-benzoxazin-6-yl)-1-methyl-1H-pyrrole-2-carbonitrile, or pharmaceutically acceptable salts thereof.

* * * * *

UNITED STATES PATENT AND TRADEMARK OFFICE
CERTIFICATE OF CORRECTION

PATENT NO. : 7,268,149 B2
APPLICATION NO. : 10/601968
DATED : September 11, 2007
INVENTOR(S) : Fensome et al.

It is certified that error appears in the above-identified patent and that said Letters Patent is hereby corrected as shown below:

Col. 4, line 54, replace "C to $C_3$" with -- $C_1$ to $C_3$ --.

Col. 18, Scheme VII, lines 5-12, replace the following reaction:

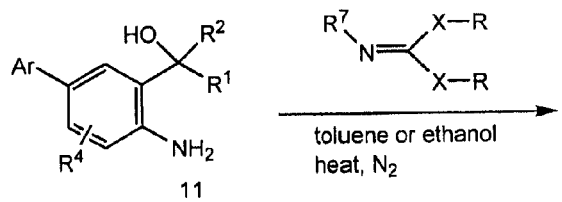

with the following reaction:

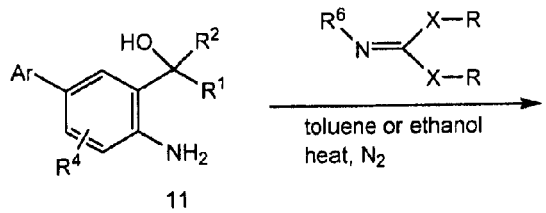

Col. 36, line 28, replace "VII" with -- µl --.

Col. 42, line 12, replace "manual" with -- mammal --.

Signed and Sealed this

Eighth Day of April, 2008

JON W. DUDAS
*Director of the United States Patent and Trademark Office*